US012692476B2

(12) United States Patent
Alon et al.

(10) Patent No.: US 12,692,476 B2
(45) Date of Patent: Jul. 28, 2026

(54) COMPOSITIONS AND METHODS FOR EMBRYONIC STEM CELL EXPANSION

(71) Applicant: LINEAGE CELL THERAPEUTICS, INC., Carlsbad, CA (US)

(72) Inventors: Lilach Alon, Kfar Yona (IL); Rami Skaliter, Ness Ziona (IL); Ravid Tikotzki, Rishon Lezion (IL); Dana Hayoun Neeman, Jerusalem (IL); Ofer Wiser, Jerusalem (IL)

(73) Assignee: LINEAGE CELL THERAPEUTICS, INC., Carlsbad, CA (US)

( * ) Notice: Subject to any disclaimer, the term of this patent is extended or adjusted under 35 U.S.C. 154(b) by 668 days.

(21) Appl. No.: 18/041,174

(22) PCT Filed: Aug. 10, 2021

(86) PCT No.: PCT/US2021/045437
§ 371 (c)(1),
(2) Date: Feb. 9, 2023

(87) PCT Pub. No.: WO2022/035895
PCT Pub. Date: Feb. 17, 2022

(65) Prior Publication Data
US 2023/0313127 A1 Oct. 5, 2023

Related U.S. Application Data

(60) Provisional application No. 63/063,942, filed on Aug. 10, 2020.

(51) Int. Cl.
*C12N 5/00* (2006.01)
*C12N 5/0735* (2010.01)

(52) U.S. Cl.
CPC ......... *C12N 5/0075* (2013.01); *C12N 5/0606* (2013.01); *C12N 2531/00* (2013.01); *C12N 2533/52* (2013.01)

(58) Field of Classification Search
None
See application file for complete search history.

(56) References Cited

U.S. PATENT DOCUMENTS

| | | | |
|---|---|---|---|
| 5,166,065 | A | 11/1992 | Williams et al. |
| 5,332,672 | A | 7/1994 | Conover et al. |
| 5,405,772 | A | 4/1995 | Ponting |
| 5,453,357 | A | 9/1995 | Hogan |
| 5,583,016 | A | 12/1996 | Villeponteau |
| 5,843,780 | A | 12/1998 | Thomson |
| 5,914,268 | A | 6/1999 | Keller et al. |
| 5,922,567 | A | 7/1999 | Young et al. |
| 5,922,597 | A | 7/1999 | Verfaillie et al. |
| 5,968,829 | A | 10/1999 | Carpenter |
| 6,090,622 | A | 7/2000 | Gearhart et al. |
| 6,200,806 | B1 | 3/2001 | Thomson |
| 6,280,718 | B1 | 8/2001 | Kaufman et al. |
| 6,458,589 | B1 | 10/2002 | Rambhatla et al. |
| 6,576,464 | B2 | 6/2003 | Gold et al. |
| 6,642,048 | B2 | 11/2003 | Xu et al. |
| 6,800,480 | B1 | 10/2004 | Bodnar et al. |
| 6,833,269 | B2 | 12/2004 | Carpenter |
| 6,875,607 | B1 | 4/2005 | Reubinoff et al. |
| 7,005,252 | B1 | 2/2006 | Thomson |
| 7,041,438 | B2 | 5/2006 | Carpenter et al. |
| 7,297,539 | B2 | 11/2007 | Mandalam et al. |
| 7,410,789 | B2 | 8/2008 | Schloesser et al. |
| 7,410,798 | B2 | 8/2008 | Mandalam et al. |
| 7,413,904 | B2 | 8/2008 | Gold et al. |
| 7,455,983 | B2 | 11/2008 | Xu et al. |
| 7,473,555 | B2 | 1/2009 | Mandalam et al. |
| 7,790,456 | B2 | 9/2010 | Terstegge et al. |
| 8,968,994 | B2 | 3/2015 | Crook et al. |
| 9,005,965 | B2 | 4/2015 | Shushan et al. |
| 9,040,297 | B2 | 5/2015 | Amit et al. |
| 9,074,181 | B2 | 7/2015 | Mandalam et al. |
| 9,732,128 | B2 | 8/2017 | West et al. |
| 9,969,972 | B2 | 5/2018 | Nelson |
| 10,676,714 | B2 | 6/2020 | Mandalam et al. |
| 10,745,752 | B2 | 8/2020 | West et al. |
| 10,920,191 | B2 | 2/2021 | West et al. |
| 11,198,849 | B2 | 12/2021 | Crook et al. |
| 12,441,983 | B2 | 10/2025 | Mandalam et al. |
| 2002/0081724 | A1 | 6/2002 | Carpenter et al. |
| 2003/0113910 | A1 | 6/2003 | Levanduski |
| 2003/0153082 | A1 | 8/2003 | Bhatia |

(Continued)

FOREIGN PATENT DOCUMENTS

| | | |
|---|---|---|
| CA | 2877233 A1 | 7/2000 |
| CN | 1424394 A | 6/2003 |

(Continued)

OTHER PUBLICATIONS

Lam et al. "Integrated processes for expansion and differentiation of human pluripotent stem cells in suspended microcarriers cultures" (2016), Biochem Biophys Res Comm, vol. 473: 764-768. (Year: 2016).*

International Preliminary Report on Patentability for PCT Application No. PCT/US2021/045437, mailed on Feb. 7, 2023, 10 pages.

International Search Report and Written Opinion for International Application No. PCT/US2021/045437, mailed on Jan. 5, 2022, 13 pages.

Abranches et al. (2007) "Expansion of Mouse Embryonic Stem Cells on Microcarriers", Biotechnology and Bioengineering, 96(6):1211-1121.

Tang et al. (2011) "An Antibody Against SSEA-5 Glycan on Human Pluripotent Stem Cells Enables Removal of Teratoma-forming Cells", Nature Biotechnology, 29(9):829-834.

Thomson et al. (Nov. 6, 1998) "Embryonic Stem Cell Lines Derived from Human Blastocysts", Science, 282 (5391):1145-1147.

(Continued)

*Primary Examiner* — Teresa E Knight
(74) *Attorney, Agent, or Firm* — Fenwick & West LLP; Matthew Pavao

(57) ABSTRACT

Provided herein are methods and compositions for expansion of human embryonic stem with suspendable expansion complexes including microcarriers.

18 Claims, 11 Drawing Sheets

(56) References Cited

U.S. PATENT DOCUMENTS

| | | |
|---|---|---|
| 2003/0224411 A1 | 12/2003 | Stanton et al. |
| 2004/0071672 A1 | 4/2004 | Hogan |
| 2005/0037492 A1 | 2/2005 | Xu et al. |
| 2005/0037493 A1 | 2/2005 | Mandalam et al. |
| 2005/0095708 A1 | 5/2005 | Pera et al. |
| 2005/0158852 A1 | 7/2005 | Wang et al. |
| 2005/0164377 A1 | 7/2005 | Miyabayashi et al. |
| 2005/0233446 A1 | 10/2005 | Parsons et al. |
| 2005/0282272 A1 | 12/2005 | Bhatia et al. |
| 2007/0264713 A1 | 11/2007 | Terstegge et al. |
| 2010/0203633 A1 | 8/2010 | Mandalam et al. |
| 2010/0317101 A1 | 12/2010 | Mandalam et al. |
| 2011/0177594 A1 | 7/2011 | Shushan et al. |
| 2012/0009645 A1 | 1/2012 | Oh et al. |
| 2012/0220031 A1 | 8/2012 | Sekiguchi et al. |
| 2013/0011918 A1 | 1/2013 | West et al. |
| 2013/0115673 A1 | 5/2013 | West et al. |
| 2015/0307838 A1 | 10/2015 | Mandalam et al. |
| 2018/0135018 A1 | 5/2018 | West et al. |
| 2018/0170982 A1 | 6/2018 | West et al. |
| 2018/0265842 A1 | 9/2018 | Nelson |
| 2020/0399592 A1 | 12/2020 | Mandalam et al. |
| 2021/0102251 A1 | 4/2021 | West et al. |

FOREIGN PATENT DOCUMENTS

| | | |
|---|---|---|
| CN | 1483817 A | 3/2004 |
| CN | 1545549 A | 11/2004 |
| CN | 1626651 A | 6/2005 |
| EP | 0695351 B1 | 12/1999 |
| WO | WO 1994/007997 A1 | 4/1994 |
| WO | WO 1997/021802 A1 | 6/1997 |
| WO | WO 1997/047734 A1 | 12/1997 |
| WO | WO 1998/030678 A1 | 7/1998 |
| WO | WO 1998/030679 A1 | 7/1998 |
| WO | WO 1998/043679 A1 | 10/1998 |
| WO | WO 1999/042122 A1 | 8/1999 |
| WO | WO 1999/043785 A1 | 9/1999 |
| WO | WO 2000/017323 A1 | 3/2000 |
| WO | WO 2001/051610 A1 | 7/2001 |
| WO | WO 2001/066697 A2 | 9/2001 |
| WO | WO 2002/031123 A1 | 4/2002 |
| WO | WO 2003/038070 A1 | 5/2003 |
| WO | WO 2003/050251 A2 | 1/2004 |
| WO | WO 2004/007696 A2 | 1/2004 |
| WO | WO 2004/055155 A2 | 7/2004 |
| WO | WO 2005/007799 A2 | 1/2005 |
| WO | WO 2005/033298 A1 | 4/2005 |
| WO | WO 2005/053601 A2 | 6/2005 |
| WO | WO 2005/065354 A2 | 7/2005 |
| WO | WO 2006/017370 A2 | 2/2006 |
| WO | WO 2006/027229 A1 | 3/2006 |
| WO | WO 2006/070370 A2 | 7/2006 |
| WO | WO 2008/004990 A2 | 1/2008 |
| WO | WO 2008/015682 A2 | 2/2008 |
| WO | 2009116951 A2 | 9/2009 |
| WO | WO 2024/102777 A2 | 5/2024 |

OTHER PUBLICATIONS

Yamanaka, S. (Jun. 7, 2007) "Strategies and New Developments in the Generation ofStem Cells", Cell Stem Cell, 1(1):39-49.

Extended European Search Report Received in EP Application No. 21856597.6, mailed on Sep. 23, 2024, 11 pages.

Cherian et al. (May 2020) "Biological Considerations in Scaling up Therapeutic Cell Manufacturing", Frontiers in Pharmacology, 11:654(25 pages).

Lam et al. (Apr. 2015) "Improved Human Pluripotent Stem Cell Attachment and Spreading on Xeno-Free Laminin-521-Coated Microcarriers Results in Efficient Growth in Agitated Cultures", Bioresearch Open Access, 4(1):242-257.

Miyazaki et al. (Jan. 20, 2017) "Efficient Adhesion Culture of Human Pluripotent Stem Cells Using Laminin Fragments in an Uncoated Manner", Scientific Reports, 7(1):8 pages.

Reubinoff et al. (Apr. 2000) "Embryonic Stem Cell Lines From Human Blastocysts: Somatic Differentiation in Vitro", Nature Biotechnology, 18(4):399-404.

Silva et al. (May 15, 2015) "Robust Expansion of Human Pluripotent Stem Cells: Integration of Bioprocess Design With Transcriptomic and Metabolomic Characterization: hPSC Expansion Bioprocess and "Omics" Tools", Stem Cells Translational Medicine, 4(7):731-742.

Al-Obeidi et al. "Development of Inhibitors for Protein Tyrosine Kinases", Oncogene, 2000, 19(49): pp. 5690-5701.

Amit et al. "Clonally Derived Human Embryonic Stem Cell Lines Maintain Pluripotency and Proliferative Potential for Prolonged Periods of Culture", Developmental Biology, Nov. 2000, 227(2): pp. 271-278.

Amit et al. "Feeder Layer-and Serum-Free Culture of Human Embryonic Stem Cells", Biology of Reproduction, Nov. 19, 2003, 70(3): pp. 837-845.

Amit et al. "Human Feeder Layers for Human Embryonic Stem Cells", Biology of Reproduction, Jun. 1, 2003, 68 (6): pp. 2150-2156.

Anzai et al. "Self-Renewal and Differentiation of a Basic Fibroblast Growth Factor-Dependent Multipotent Hematopoietic Cell Line Derived from Embryonic Stem Cells", Development Growth & Differentiation, Feb. 1999, 41 (1):51-58.

Beattie et al. "Activin A Maintains Pluripotency of Human Embryonic Stem Cells in the Absence of Feeder Layers", Stem Cells, 2005, 23(4): pp. 489-495.

Berger et al. "Self Renewal of Embryonic Stem Cells in the Absence of Feeder Cells and Exogenous Leukaemia Inhibitory Factor", Growth Factors, 1997, 14(2-3) pp. 145-159.

Brook et al. "The Origin and Efficient Derivation of Embryonic Stem Cells in the Mouse", Proceedings of the National Academy of Sciences of the United States of America, May 1997, 94(11): pp. 5709-5712.

Cambridge Dictionary, Entry for "undifferentiated", 3 Pages. [Retrieved on Mar. 31, 2026] Retrieved from the internet <URL: dictionary. cambridge.org/us/dictionary/english/undifferentiated>.

Carpenter et al. "Enrichment of Neurons and Neural Precursors from Human Embryonic Stem Cells", Experimental Neurology, Dec. 2001, 172(2): pp. 383-397.

Carpenter et al. "Properties of Four Human Embryonic Stem Cell Lines Maintained in a Feeder-Free Culture System", Developmental Dynamics, 2004, 229(2): pp. 243-258.

Chambers et al. "Functional Expression Cloning of Nanog, a Pluripotency Sustaining Factor in Embryonic Stem Cells", Cell, May 30, 2003, 113(5): pp. 643-655.

Chen et al. "Critical microcarrier properties affecting the expansion of undifferentiated human embryonic stem cells", Stem Cell Research, May 11, 2011, 7: pp. 97-111.

Cheng et al. "Human Adult Marrow Cells Support Prolonged Expansion of Human Embryonic Stem Cells in Culture", Stem Cells, 2003, 21(2):pp. 131-142.

Chung et al. "Human Embryonic Stem Cell Lines Generated without Embryo Destruction", Cell Stem Cell, Feb. 7, 2008, 2(2):113-117.

Corning, "Corning Matrigel Matrix" 2023, 8 pages, <URL: corning. com/catalog/cls/documents/faqs/CLS-DL-CC-026.pdf>, 8 pages provided.

Coutu et al. "Roles of FGF Signaling In Stem Cell Self-Renewal, Senescence and Aging", Aging, Oct. 9, 2011, 3 (10): pp. 920-933.

Dalton et al. "Stem Cell Chemistry", 2005, 6 pages. <URL:cen.acs. org/articles/83/i7/STEM-CELL-CHEMISTRY.html>.

Dang et al. (2004) "Controlled, Scalable Embryonic Stem Cell Differentiation Culture", Stem Cells, 22(3): pp. 275-282.

Denning et al. "Common Culture Conditions for Maintenance and Cardiomyocyte Differentiation of the Human Embryonic Stem Cell Lines, BG01 and HUES-7", The International Journal of Developmental Biology, Feb. 2006, 50 (1): pp. 27-37.

Domínguez-Bendala et al. "Islet Cell Therapy and Pancreatic Stem Cells", Handbook of Stem Cells, 2013, Chapter 70, pp. 835-853.

(56)        References Cited

OTHER PUBLICATIONS

Dravid et al. "Defining the Role of Wnt/β-Catenin Signaling in the Survival, Proliferation, and Self-Renewal of Human Embryonic Stem Cells", Stem Cells, 2005, 23(10): pp. 1489-1501.

Drukker et al. "Genetic manipulation of human embryonic stem cells", Human Embryonic Stem Cells, 2003, pp. 265-284.

Dvorak et al. "Expression and Potential Role of Fibroblast Growth Factor 2 and Its Receptors in Human Embryonic Stem Cells", Stem Cells, 2005, 23(8): pp. 1200-1211.

Eiges et al. "Establishment of Human Embryonic Stem Cell-Transfected Clones Carrying a Marker for Undifferentiated Cells", Current Biology, Apr. 3, 2001, 11(7): pp. 514-518.

Evans et al. "Establishment in Culture of Pluripotential Cells from Mouse Embryos", Nature, Jul. 1981, 292 (5819): pp. 154-156.

Fok et al. "Shear-Controlled Single-Step Mouse Embryonic Stem Cell Expansion and Embryoid Body-Based Differentiation", Stem Cells, Aug. 4, 2005, 23(9): pp. 1333-1342.

Fok, "Development of a scalable bioprocess for the culture of undifferentiated murine embryonic stem cells", Thesis submitted for Master of Applied Science degree, University of Toronto, 2004, pp. 1-103; w front matter p. i-ix; and appendix matter A-1 to A-3, 116 pages provided.

Genbacev et al. "Serum-Free Derivation of Human Embryonic Stem Cell Lines on Human Placental Fibroblast Feeders", Fertility and Sterility, 2005, 83(5): pp. 1517-1529.

Gendall et al. "Isolation and Characterization of a Leukemia Inhibitory Factor-Independent Embryonic Stem Cell Line", The International Journal of Biochemistry & Cell Biology, May 1997, 29 (5): pp. 829-840.

Gerecht-Nir et al. "Bioreactor Cultivation Enhances the Efficiency of a Human Embryoid Body (Heb Formation and Differentiation", Biotechnology and Bioengineering, Jun. 5, 2004, 86(5): pp. 493-502.

Guo et al. "Naive Pluripotent Stem Cells Derived Directly from Isolated Cells of the Human Inner Cell Mass", Stem Cell Reports, Apr. 12, 2016, 6(4): pp. 437-446.

Heike et al. "Ex vivo expansion of hematopoietic stem cells by cytokines" Biochimica et Biophysica Acta, Nov. 11, 2002, 1592, pp. 313-321.

Hoffman et al. "Characterization and culture of human embryonic stem cells," Nature Biotechnology Jun. 2005 vol. 23, No. 6, pp. 699-708.

Hovatta et al. "A Culture System Using Human Foreskin Fibroblasts as Feeder Cells Allows Production of Human Embryonic Stem Cells", Human Reproduction, 2003, 18(7): pp. 1404-1409.

IMATRIX-511 "Wako Bio Window" 147, Nov. 2016, 11(147): 36 Pages, machine translation of p. 8 provided.

Itskovitz-Eldor et al. "Differentiation of Human Embryonic Stem Cells into Embryoid Bodies Compromising the Three Embryonic Germ Layers", Molecular Medicine, Feb. 2000, 6(2): pp. 88-95.

James et al. "TGFβ/Activin/Nodal Signaling is Necessary for the Maintenance of Pluripotency in Human Embryonic Stem Cells", Development, 2005, 132(6): pp. 1273-1282.

Kehat et al. "Human Embryonic Stem Cells can Differentiate into Myocytes with Structural and Functional Properties of Cardiomyocytes", Journal of Clinical Investigation, Aug. 2001, 108(3): pp. 407-414.

Kehoe et al. "Scalable Stirred-Suspension Bioreactor Culture of Human Pluripotent Stem Cells", Tissue Engineering: Part A, Oct. 17, 2009, 16(2): pp. 405-421.

Keirstead et al. "Human Embryonic Stem Cell-Derived Oligodendrocyte Progenitor Cell Transplants Remyelinate and Restore Locomotion After Spinal Cord Injury", The Journal of Neuroscience, May 11, 2005, 25(19): pp. 4694-4705.

Keller, "In Vitro Differentiation of Embryonic Stem Cells", Current Opinion in Cell Biology, Dec. 1995, 7(6): pp. 862-869.

Klimanskaya et al. "Human Embryonic Stem Cell Lines Derived from Single Blastomeres", Nature, Nov. 23, 2006, 444(7118): pp. 481-485.

Klimanskaya et al. "Human Embryonic Stem Cells Derived without Feeder Cells", Lancet, Mar. 8, 2005, 35 (9471): pp. 1636-1641.

Koshimizu et al. "Functional Requirement of Gp130-Mediated Signaling for Growth and Survival of Mouse Primordial Germ Cells in Vitro and Derivation of Embryonic Germ (EG) Cells", Development, 1996, 122(4): pp. 1235-1242.

Koshimizu et al. "Retinoic Acid Is a Potent Growth Activator of Mouse Primordial Germ Cells in Vitro", Developmental Biology, 1995, 168(2): pp. 683-685.

Kurosawa et al. "Methods for Inducing Embryoid Body Formation: In Vitro Differentiation System of Embryonic Stem Cells", Journal of Bioscience And Bioengineering, May 2007, 103(5): pp. 389-398.

Lai et al. "SRY (Sex Determining Region Y)-Box2 (Sox2)/Poly ADP-Ribose Polymerase 1 (Parp1) Complexes Regulate Pluripotency", Proceedings of the National Academy of Sciences of the United States of America, Mar. 6, 2012, 109(10): pp. 3772-3777.

Lebkowski et al. "Human Embryonic Stem Cells: Culture, Differentiation, and Genetic Modification for Regenerative Medicine Applications", The Cancer Journal, 2001, (Suppl 2): pp. S83-S93.

Levenstein et al. "Basic FGF Support of Human Embryonic Stem Cell Self-Renewal", Stem Cells, Mar. 2006, 24(3):16 Pages.

Li et al. "Expansion of Human Embryonic Stem Cells in Defined Serum-Free Medium Devoid of Animal-Derived Products", Biotechnology and Bioengineering, Jun. 21, 2005, 91(6): pp. 688-698.

Lim et al. "Proteome Analysis of Conditioned Medium From Mouse Embryonic Fibroblast Feeder Layers Which Support the Growth of Human Embryonic Stem Cells", Proteomics, Sep. 2002, 2(9): pp. 1187-1203.

Ludwig et al. "Derivation of Human Embryonic Stem Cells In Defined Conditions", Nature Biotechnology, Jan. 1, 2006, 24(2): pp. 185-187.

Matsuda et al. "STAT3 Activation is Sufficient to Maintain an Undifferentiated State of Mouse Embryonic Stem Cells", The EMBO Journal, 1999, 18(15): pp. 4261-4269.

Matsui et al. "Derivation of Pluripotential Embryonic Stem Cells from Murine Primordial Germ Cells in Culture", Cell, Sep. 4, 1992, 70(5): pp. 841-847, 14 pages provided, with English Abstract.

Mered et al. "Cell Growth Optimization In Microcarrier Culture", In Vitro, Oct. 1980, 16(10): pp. 859-865.

Merriam-Webster's Dictionary, Entry for "pluripotent", 3 Pages. [Online] [Retrieved on Mar. 30, 2026] Retrieved from the internet <URL: www.merriam-webster.com/dictionary/pluripotent>.

Mitsui et al. "The Homeoprotein Nanog is Required for Maintenance of Pluripotency in Mouse Epiblast and ES Cells", Cell, May 30, 2003, 13(5): pp. 631-642.

Miyamoto et al. "Human Placenta Feeder Layers Support Undifferentiated Growth of Primate Embryonic Stem Cells", Stem Cells, 2004, 22(4): pp. 433-440.

Nichols et al. "Derivation of Germline Competent Embryonic Stem Cells with a Combination of Interleukin-6 and Soluble Interleukin-6 Receptor", Experimental Cell Research, Nov. 1994, 215(1): pp. 237-239.

Nichols et al. "Establishment of Germ-Line-Competent Embryonic Stem (ES) Cells Using Differentiation Inhibiting Activity", Development, 1990, 110(4): pp. 1341-1348.

Oh et al. "Human Embryonic Stem Cells: Technological Challenges towards Therapy", Clinical and Experimental Pharmacology and Physiology, 2006, 33: pp. 489-495.

Ornitz et al. "Fibroblast Growth Factors", Genome Biology, Mar. 9, 2001, 2(3): pp. 1-12.

Pandey et al. "End-to-End Platform for Human Pluripotent Stem Cell Manufacturing", International Journal of Molecular Sciences, Dec. 21, 2019, 29 Pages.

Pease et al. "Isolation of Embryonic Stem (ES) Cells In Media Supplemented With Recombinant Leukemia Inhibitory Factor (LIF)", Developmental Biology, Oct. 1990, 141(2): pp. 344-352.

Pébay et al. "Essential Roles of Sphingosine-1-Phosphate and Platelet-Derived Growth Factor in the Maintenance of Human Embryonic Stem Cells", Stem Cells, 2005, 23(10): pp. 1541-1548.

Pera et al. "Gene Expression Profiles of Human Inner Cell Mass Cells and Embryonic Stem Cells", Differentiation, Jul. 2009, 78(1): pp. 18-23.

Prowse et al. "A Proteome Analysis of Conditioned Media from Human Neonatal Fibroblasts Used in the Maintenance of Human Embryonic Stem Cells", Proteomics, Mar. 2005, 5(4): pp. 978-989.

(56)                    References Cited

OTHER PUBLICATIONS

Pyle et al. "Neurotrophins Mediate Human Embryonic Stem Cell Survival", Nature Biotechnology, Jan. 29, 2006, 24(3): pp. 344-350.
Richards et al. "Comparative Evaluation of Various Human Feeders for Prolonged Undifferentiated Growth of Human Embryonic Stem Cells", Stem Cells, 2003, 21(5): pp. 546-556.
Richards et al. "Human Feeders Support Prolonged Undifferentiated Growth of Human Inner Cell Masses and Embryonic Stem Cells", Nature Biotechnology, Sep. 2002, 20(9): pp. 933-936.
Robertson, "Derivation and Maintenance of Embryonic Stem Cell Cultures", Methods in Molecular Biology, 1997, 75: pp. 173-184.
Rose et al. "Oncostatin M (OSM) Inhibits the Differentiation of Pluripotent Embryonic Stem Cells In Vitro", Cytokine, Jan. 1994, 6(1): pp. 48-54.
Rosler et al. "Long-Term Culture of Human Embryonic Stem Cells in Feeder-Free Conditions", Developmental Dynamics, Feb. 2004, 229(2): pp. 259-274.
Sato et al. "Maintenance of Pluripotency in Human and Mouse Embryonic Stem Cells Through Activation of Wnt Signaling by a Pharmacological GSK-3-Specific Inhibitor", Nature Medicine, Jan. 2004, 10(1): pp. 55-63.
Schechter et al. "Growth of Purified Lacrimal Acinar Cells in Matrigel Raft Cultures", Experimental Eye Research, 2002, 74(3): pp. 349-360.
Schulz et al. "Differentiation of Human Embryonic Stem Cells to Dopaminergic Neurons in Serum-Free Suspension Culture", Stem Cells, 2004, 22(7): pp. 1218-1238.
Shamblott et al. "Derivation of Pluripotent Stem Cells from Cultured Human Primordial Germ Cells", Proceedings of the National Academy of Sciences of the United States of America, Nov. 1998, 95(23): pp. 13726-13731.
Shamblott et al. "Human Embryonic Germ Cell Derivatives Express a Broad Range of Developmentally Distinct Markers and Proliferate Extensively In Vitro", Proceedings of the National Academy of Sciences of the United States of America, Jan. 2, 2001, 98(1): pp. 113-118.
Smith et al. "Inhibition of Pluripotential Embryonic Stem Cell Differentiation by Purified Polypeptides", Nature, Dec. 15, 1988, 336(6200): pp. 688-690.
Sottile et al. "In Vitro Osteogenic Differentiation of Human ES Cells", Cloning & Stem Cells, 2003, 5(2): pp. 149-155.
Stojkovic et al. "An Autogeneic Feeder Cell System That Efficiently Supports Growth of Undifferentiated Human Embryonic Stem Cells", Stem Cells, Mar. 2005, 23(3): pp. 306-314.
Stojkovic et al. "Derivation, Growth and Applications of Human Embryonic Stem Cells", Reproduction, 2004, 128(3): pp. 259-267.
Strelchenko et al. "Embryonic Stem Cells from Morula", Methods in Enzymology, 2006, 418: pp. 93-108.
Thomson et al. "Isolation of a Primate Embryonic Stem Cell Line", Proceedings of the National Academy of Sciences of the United States of America, Aug. 1995, 92(17): pp. 7844-7848.
Thomson et al. "Primate Embryonic Stem Cells", Current Topics in Developmental Biology, 1998, 38: pp. 133-165.
Trosko et al. "Gap Junctions and the Regulation of Cellular Functions of Stem Cells During Development and Differentiation", Methods, 2000, 20(2): pp. 245-264.

Tsukada et al. "Acidic Fibroblast Growth Factor Promotes Hepatic Differentiation of Monkey Embryonic Stem Cells", In Vitro Cellular & Developmental Biology—Animal, 2006, 41: pp. 83-88.
Vallier et al. "Activin/Nodal and FGF Pathways Cooperate to Maintain Pluripotency of Human Embryonic Stem Cells", Journal of Cell Science, 2005, 118(Pt 19): pp. 4495-4509.
Vallier et al. "Nodal Inhibits Differentiation of Human Embryonic Stem Cells Along the Neuroectodermal Default Pathway", Developmental Biology, Sep. 22, 2004, 275(2): pp. 403-421.
Vassiliieva et al. "Establishment of SSEA-1- and Oct-4-Expressing Rat Embryonic Stem-like Cell Lines and Effects of Cytokines of the IL-6 Family on Clonal Growth", Experimental Cell Research, Aug. 1, 2000, 258(2): pp. 361-373.
Wang et al. "Derivation and Growing Human Embryonic Stem Cells on Feeders Derived from Themselves", Stem Cells, Jun. 13, 2005, 23(9): pp. 1221-1227.
Wang et al. "Noggin and Bfgf Cooperate to Maintain the Pluripotency of Human Embryonic Stem Cells in the Absence of Feeder Layers", Biochemical and Biophysical Research Communications, May 13, 2005, 330(3): pp. 934-942.
Wartenberg et al. "Tumor-induced Angiogenesis Studied in Confrontation Cultures of Multicellular Tumor Spheroids and Embryoid Bodies Grown From Pluripotent Embryonic Stem Cells", FASEB Journal, 2001, 15(6): pp. 995-1005.
Williams et al. "Myeloid Leukaemia Inhibitory Factor Maintains the Developmental Potential of Embryonic Stem Cells", Nature, Dec. 15, 1988, 336(6200): pp. 684-687.
Xiao et al. "Activin A Maintains Self-Renewal and Regulates Fibroblast Growth Factor, Wnt, and Bone Morphogenic Protein Pathways in Human Embryonic Stem Cells", Stem Cells, Feb. 2, 2006, 24(6): pp. 1476-1486.
Xu et al. "Basic FGF and Suppression of BMP Signaling Sustain Undifferentiated Proliferation of Human ES Cells", Nature Methods, Mar. 2005, 2(3): pp. 185-190.
Xu et al. "Basic Fibroblast Growth Factor Supports Undifferentiated Human Embryonic Stem Cell Growth Without Conditioned Medium", Stem Cells, Mar. 2005, 23(3): pp. 315-323.
Xu et al. "Characterization and Enrichment of Cardiomyocytes Derived from Human Embryonic Stem Cells", Circulation Research, Sep. 20, 2002, 91(6): pp. 501-508.
Xu et al. "Feeder-Free Growth of Undifferentiated Human Embryonic Stem Cells", Nature Biotechnology, Oct. 1, 2001, 19(10): pp. 971-974.
Xu et al. "Immortalized Fibroblast-Like Cells Derived from Human Embryonic Stem Cells Support Undifferentiated Cell Growth", Stem Cells, 2004, 22(6): pp. 972-980.
Yan et al. "Single-Cell RNA-Seq Profiling of Human Preimplantation Embryos and Embryonic Stem Cells", Nature Structural & Molecular Biology, Sep. 2013, 20(9): pp. 1131-1139.
Zandstra et al. "Leukemia Inhibitory Factor (LIF) Concentration Modulates Embryonic Stem Cell Self Renewal and Differentiation Independently of Proliferation", Biotechnology and Bioengineering, 2000, 69(6): pp. 607-617.
Zwaka et al. "Genetic Modification of Human Embryonic Stem Cells", Embryonic Stem Cells, Eds. Springer, 2007, pp. 41-52.

* cited by examiner

Group 1.2

Group 1.1

COMPOSITIONS AND METHODS FOR EMBRYONIC STEM CELL EXPANSION

CROSS-REFERENCE TO RELATED APPLICATION

This application claims the benefit of U.S. Provisional Application No. 63/063,942, filed Aug. 10, 2020, which is incorporated herein by reference in its entirety and for all purposes.

BACKGROUND

Human embryonic stem cells (hESC) have a basic property of self-renewal, which makes them an unlimited cell source and enables industrial-scale cell therapy initiatives. Their pluripotent developmental potential positioned them as a cell source for most cell therapy products.

A critical requirement for hESC clinical applications is the supply of a large quantity of hESC-derived therapeutic cells. Production of these therapeutic cells starts from thawing cells of qualified cell banks, such as the master cell bank (MCB) or the working cell bank (WCB), under current good manufacturing practices (cGMP). The quality of the cell bank plays an important role in hESC bioprocessing as it impacts post-thaw hESC expansion, the efficiency of the subsequent lineage-specific differentiation, and process reproducibility.

Manufacturing such a cell bank is labor intensive, usually requires manual cell manipulations, and there is lot-to-lot variability due to several critical raw materials such as the use of feeder cells, non-recombinant matrix, serum and other materials which are not fully defined.

BRIEF SUMMARY

To make such cell therapy initiatives a reality, provided herein are methods for the production of GMP grade hESCs or human-induced pluripotent stem cells (hiPSCs) banks.

In one aspect, the present disclosure provides a method for expanding and maintaining human embryonic stem cells (hESCs) in an undifferentiated, pluripotent state, the method comprising the steps of (a) simultaneously combining human embryonic stem cells, an extracellular matrix component (ECM), and a microcarrier in growth media to form a suspendable expansion complex, and (b) culturing the suspendable expansion complex for a period of time.

In some embodiments, the microcarriers comprise one or more of polystyrene, cross-linked dextran, magnetic particles, microchips, cellulose, hydroxylated methacrylate, collagen, gelatin, polystyrene, plastic, glass, ceramic, silicone, or a combination thereof.

In some embodiments, the microcarriers are spherical, smooth, macroporous, rod-shaped, or a combination thereof.

In some embodiments, the ECM comprises matrigel, laminin, vitronectin, collagen, their derivatives, or a combination thereof. In specific embodiments, the ECM is human laminin In specific embodiments, the human laminin is human laminin 511 E8 fragment.

In specific embodiments, the microcarriers are not coated.

In some embodiments, the microcarriers are coupled with protamine or polylysine.

In some embodiments, the microcarriers are neutral or negatively charged. In specific embodiments, the microcarriers are neutral. In specific embodiments, the microcarriers are negatively charged. In specific embodiments, the microcarriers are hydrophilic.

In some embodiments, the suspendable expansion complex is cultured for at least about one day. In some embodiments, the suspendable expansion complex is cultured from about one day to about fourteen days.

In some embodiments, the cultured cells of the suspendable expansion complex are harvested and expanded further by repeating steps (a) and (b).

In some embodiments, the cultured cells of the suspendable expansion complex are harvested and further differentiated. In some embodiments, the cultured cells of the suspendable expansion complex are further differentiated by changing the growth medium.

In some embodiments, the cultured cells of the suspendable expansion complex remain undifferentiated and pluripotent. In some embodiments, the undifferentiated cells express at least about 80% of each of SSEA-5 and TRA-1-60. In some embodiments, the undifferentiated cells express at least about 70% of each of Oct-4 and Nanog. In some embodiments, the undifferentiated cells express at least about 80% of SSEA-5, at least about 80% of TRA-1-60, at least about 70% of Oct-4, and at least about 70% of Nanog.

In another aspect, the present disclosure provides a suspendable expansion complex composition comprising human embryonic stem cells, an extracellular matrix component (ECM), and a microcarrier.

In some embodiments, the composition further comprises a growth medium.

In some embodiments, the microcarriers comprise one or more of polystyrene, cross-linked dextran, magnetic particles, microchips, cellulose, hydroxylated methacrylate, collagen, gelatin, polystyrene, plastic, glass, ceramic, silicone. In some embodiments, the microcarriers are spherical, smooth, macroporous, rod-shaped, or a combination thereof.

In some embodiments, the microcarriers are coated with matrigel, laminin, vitronectin, collagen, their derivatives, or a combination thereof. In some embodiments, the laminin is human laminin In specific embodiments, the human laminin is human laminin 511 E8 fragment.

In some embodiments, the microcarriers are not coated.

In some embodiments, the microcarriers are coupled with protamine or polylysine.

In some embodiments, the microcarriers are neutral or negatively charged. In some embodiments, the microcarriers are neutral. In some embodiments, the microcarriers are negatively charged. In some embodiments, the microcarriers are hydrophilic.

DETAILED DESCRIPTION

Figure 1:
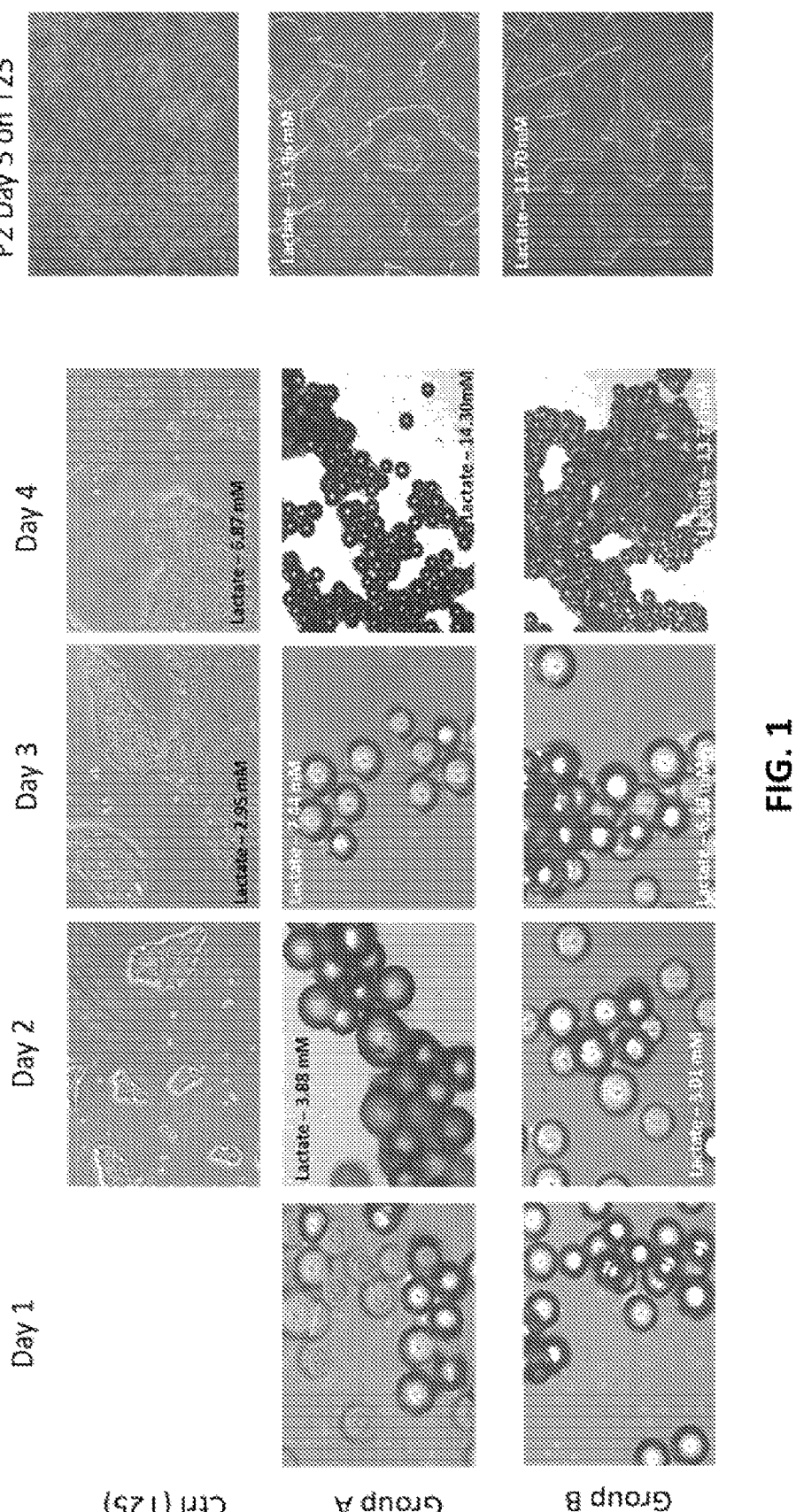
FIG. 1 shows morphology assessment along passage. P1 on MC Group A-Synthemax® II MC, Group B-Enhanced Attachment MC. Cells grown on MC were harvested and seeded for P2 on TC treated T25 flasks.

Embodiments herein generally relate to methods, compositions of matter, and devices for expanding embryonic stem cells.

After reading this description it will become apparent to one skilled in the art how to implement the present disclosure in various alternative embodiments and alternative applications. However, all the various embodiments of the present invention will not be described herein. It will be understood that the embodiments presented here are presented by way of an example only, and not limitation. As such, this detailed description of various alternative embodiments should not be construed to limit the scope or breadth of the present disclosure as set forth herein.

Before the present technology is disclosed and described, it is to be understood that the aspects described below are not limited to specific compositions, methods of preparing such compositions, or uses thereof as such may, of course, vary. It is also to be understood that the terminology used herein is for the purpose of describing particular aspects only and is not intended to be limiting.

The detailed description divided into various sections only for the reader's convenience and disclosure found in any section may be combined with that in another section. Titles or subtitles may be used in the specification for the convenience of a reader, which are not intended to influence the scope of the present disclosure.

Definitions

As used herein, the singular forms "a", "an" and "the" are intended to include the plural forms as well, unless the context clearly indicates otherwise.

"Optional" or "optionally" means that the subsequently described event or circumstance can or cannot occur, and that the description includes instances where the event or circumstance occurs and instances where it does not.

The term "about" when used before a numerical designation, e.g., temperature, time, amount, concentration, and such other, including a range, indicates approximations which may vary by (+) or (−) 10%, 5%, 1%, or any subrange or subvalue there between. Preferably, the term "about" when used with regard to an amount means that the amount may vary by +/−10%.

"Comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) of the claimed invention. "Consisting of" shall mean excluding more than trace elements of other ingredients and substantial method steps. Embodiments defined by each of these transition terms are within the scope of this disclosure.

An "effective amount" is an amount sufficient for a composition to accomplish a stated purpose relative to the absence of the composition (e.g. achieve the effect for which it is administered, treat a disease, reduce enzyme activity, increase enzyme activity, reduce a signaling pathway, or reduce one or more symptoms of a disease or condition). An example of an "effective amount" is an amount sufficient to contribute to the treatment, prevention, or reduction of a symptom or symptoms of a disease, which could also be referred to as a "therapeutically effective amount." A "reduction" of a symptom or symptoms (and grammatical equivalents of this phrase) means decreasing of the severity or frequency of the symptom(s), or elimination of the symptom(s). A "prophylactically effective amount" of a drug (e.g., the cells described herein) is an amount of the drug that, when administered to a subject, will have the intended prophylactic effect, e.g., preventing or delaying the onset (or reoccurrence) of an injury, disease, pathology or condition, or reducing the likelihood of the onset (or reoccurrence) of an injury, disease, pathology, or condition, or their symptoms. The full prophylactic effect does not necessarily occur by administration of one dose, and may occur only after administration of a series of doses. Thus, a prophylactically effective amount may be administered in one or more administrations. An "activity decreasing amount," as used herein, refers to an amount of antagonist required to decrease the activity of an enzyme relative to the absence of the antagonist. A "function disrupting amount," as used herein, refers to the amount of antagonist required to disrupt the function of an enzyme or protein relative to the absence of the antagonist. The exact amounts will depend on the purpose of the treatment, and will be ascertainable by one skilled in the art using known techniques (see, e.g., Lieberman, *Pharmaceutical Dosage Forms* (vols. 1-3, 1992); Lloyd, *The Art, Science and Technology of Pharmaceutical Compounding* (1999); Pickar, *Dosage Calculations* (1999); and *Remington: The Science and Practice of Pharmacy*, 20th Edition, 2003, Gennaro, Ed., Lippincott, Williams & Wilkins).

For any composition described herein, the therapeutically effective amount can be initially determined from cell culture assays. Target concentrations will be those concentrations of active composition(s) (e.g., cell concentration or number) that are capable of achieving the methods described herein, as measured using the methods described herein or known in the art.

"Control" or "control experiment" is used in accordance with its plain ordinary meaning and refers to an experiment in which the subjects or reagents of the experiment are treated as in a parallel experiment except for omission of a procedure, reagent, or variable of the experiment. In some instances, the control is used as a standard of comparison in evaluating experimental effects. In some embodiments, a control is the measurement of the activity of a protein in the absence of a composition as described herein (including embodiments and examples).

"Pharmaceutically acceptable excipient" and "pharmaceutically acceptable carrier" refer to a substance that aids the administration of an active agent to and absorption by a subject and can be included in the compositions of the present disclosure without causing a significant adverse toxicological effect on the patient. Non-limiting examples of pharmaceutically acceptable excipients include water, NaCl, normal saline solutions, lactated Ringer's, normal sucrose, normal glucose, binders, fillers, disintegrants, lubricants, coatings, sweeteners, flavors, salt solutions (such as Ringer's solution), alcohols, oils, gelatins, carbohydrates such as lactose, amylose or starch, fatty acid esters, hydroxymethy-cellulose, polyvinyl pyrrolidine, and colors, and the like. Such preparations can be sterilized and, if desired, mixed with auxiliary agents such as lubricants, preservatives, sta-bilizers, wetting agents, emulsifiers, salts for influencing osmotic pressure, buffers, coloring, and/or aromatic sub-stances and the like that do not deleteriously react with the compositions of the disclosure. One of skill in the art will recognize that other pharmaceutical excipients are useful in the present disclosure.

A "cell" as used herein, refers to a cell carrying out metabolic or other function sufficient to preserve or replicate its genomic DNA. A cell can be identified by well-known methods in the art including, for example, presence of an intact membrane, staining by a particular dye, ability to produce progeny or, in the case of a gamete, ability to combine with a second gamete to produce a viable offspring. Cells may include prokaryotic and eukaryotic cells. Pro-karyotic cells include but are not limited to bacteria. Eukary-otic cells include but are not limited to yeast cells and cells derived from plants and animals, for example mammalian, insect (e.g., spodoptera) and human cells. Cells may be useful when they are naturally nonadherent or have been treated not to adhere to surfaces, for example by trypsini-zation.

As used herein, the "stem cells" refers to cells which are capable of remaining in an undifferentiated state (e.g., pluripotent or multipotent stem cells) for extended periods of time in culture until induced to differentiate into other cell types having a particular, specialized function (e.g., fully differentiated cells). In embodiments, "stem cells" include embryonic stem cells (ESCs), induced pluripotent stem cells (iPSCs), adult stem cells, mesenchymal stem cells and hematopoietic stem cells.

As used herein, "induced pluripotent stem cells" or "iPSCs" are cells that can be generated from somatic cells by genetic manipulation of somatic cells, e.g., by retroviral transduction of somatic cells such as fibroblasts, hepato-cytes, gastric epithelial cells with transcription factors such as Oct-3/4, Sox2, c-Myc, and KLF4 [Yamanaka S, Cell Stem Cell. 2007, 1(1):39-49; Aoi T, et al., Generation of Pluripo-tent Stem Cells from Adult Mouse Liver and Stomach Cells. Science. 2008 Feb. 14. (Epub ahead of print); I H Park, Zhao R, West J A, et al. Reprogramming of human somatic cells to pluripotency with defined factors. Nature 2008; 451:141-146; K Takahashi, Tanabe K, Ohnuki M, et al. Induction of pluripotent stem cells from adult human fibroblasts by defined factors. Cell 2007; 131:861-872]. Other embryonic-like stem cells can be generated by nuclear transfer to oocytes, fusion with embryonic stem cells or nuclear trans-fer into zygotes if the recipient cells are arrested in mitosis. In addition, iPSCs may be generated using non-integrating methods e.g., by using small molecules or RNA.

The term "embryonic stem cells" refers to embryonic cells that are capable of differentiating into cells of all three embryonic germ layers (i.e., endoderm, ectoderm and meso-derm), or remaining in an undifferentiated state. The phrase "embryonic stem cells" comprise cells which are obtained from the embryonic tissue formed after gestation (e.g., blastocyst) before implantation of the embryo (i.e., a pre-implantation blastocyst), extended blastocyst cells (EBCs) which are obtained from a post-implantation/pre-gastrula-tion stage blastocyst (see WO 2006/040763) and embryonic germ (EG) cells which are obtained from the genital tissue of a fetus any time during gestation, preferably before 10 weeks of gestation. In embodiments, embryonic stem cells are obtained using well-known cell-culture methods. For example, human embryonic stem cells can be isolated from human blastocysts.

It is appreciated that commercially available stem cells can also be used in aspects and embodiments of the present disclosure. Human ES cells may be purchased from the NIH human embryonic stem cells registry, www.grants.nih.gov-stem_cells/ or from other hESC registries. Non-limiting examples of commercially available embryonic stem cell lines are HAD-C 102, ESI, BGO 1, BG02, BG03, BG04, CY12, CY30, CY92, CY1O, TE03, TE32, CHB-4, CHB-5, CHB-6, CHB-8, CHB-9, CHB-10, CHB-11, CHB-12, HUES 1, HUES 2, HUES 3, HUES 4, HUES 5, HUES 6, HUES 7, HUES 8, HUES 9, HUES 10, HUES 11, HUES 12, HUES 13, HUES 14, HUES 15, HUES 16, HUES 17, HUES 18, HUES 19, HUES 20, HUES 21, HUES 22, HUES 23, HUES 24, HUES 25, HUES 26, HUES 27, HUES 28, CyT49, RUES3, WAO 1, UCSF4, NYUES 1, NYUES2, NYUES3, NYUES4, NYUESS, NYUES6, NYUES7, UCLA 1, UCLA 2, UCLA 3, WA077 (H7), WA09 (H9), WA 13 (H13), WA14 (H14), HUES 62, HUES 63, HUES 64, CT I, CT2, CT3, CT4, MA135, Eneavour-2, WIBR 1, WIBR2, WIBR3, WIBR4, WIBRS, WIBR6, HUES 45, Shef 3, Shef 6, BINhem19, BJNhem20, SAGO 1, SAOO1.

As used herein, the term "microcarrier" or "MC" refers to a suspendible support matrix that allows adherent cells to grow in dynamic or static cell culture, and can stay in suspension with gentle mixing. Microcarriers can be com-posed of including, but not limited to, polystyrene, surface-modified polystyrene, chemically modified polystyrene, cross-linked dextran, cellulose, acrylamide, collagen, alg-inate, gelatin, glass, DEAE-dextran, or a combination thereof. Microcarriers can be coated with a biological sup-port matrix, including, but not limited to, laminin, Matrigel, collagen, poly-lysine, poly-L-lysine, poly-D-lysine, vit-ronectin, fibronectin, tenascin, dextran, a peptide, or a com-bination thereof. Many different types of microcarriers are commercially available, including, but not limited to, HyQ-Sphere (HyClone), Hillex (SoloHill Engineering), and Low Concentration Synthemax® II (Corning) brands. Microcar-riers can be made from cross-linked dextran such as the Cytodex brand (GE Healthcare). Microcarriers can be spherical and smooth, can have microporous surfaces, such as CYTOPORE brand (GE Healthcare), and/or can be rod-shaped carriers such as DE-53 (Whatman). Microcarri-ers can be impregnated with magnetic particles that may help in cell separation from beads (e.g., GEM particles from Global Cell Solutions). Chip-based microcarriers such as the μHex product (Nunc) provide a flat surface for cell growth while maintaining the high surface to volume ratio of traditional microcarriers. The properties of microcarriers may significantly affect expansion rates and cell multi- or pluripotency.

Methods

In an aspect, provided herein are methods for expanding and maintaining human embryonic stem cells (hESCs) in an undifferentiated, pluripotent state, the method comprising the steps of (a) simultaneously combining human embryonic stem cells, an extracellular matrix component (ECM), and a microcarrier in growth media to form a suspendable expan-sion complex, and (b) culturing the suspendable expansion complex for a period of time.

In some embodiments, the cultured cells of the suspend-able expansion complex are harvested and expanded further by repeating steps (a) and (b).

In some embodiments, the cultured cells of the suspendable expansion complex are harvested and further differentiated.

Human embryonic stem cells can be isolated from human blastocysts. Human blastocysts are typically obtained from human in vivo preimplantation embryos or from in vitro fertilized (IVF) embryos. Alternatively, a single cell human embryo can be expanded to the blastocyst stage. For the isolation of human ES cells the zona pellucida is removed from the blastocyst and the inner cell mass (ICM) is isolated by a procedure in which the trophectoderm cells are lysed and removed from the intact ICM by gentle pipetting. The ICM is then plated in a tissue culture flask containing the appropriate medium which enables its outgrowth. Following 9 to 15 days, the ICM derived outgrowth is dissociated into clumps either by a mechanical dissociation or by an enzymatic degradation and the cells are then re-plated on a fresh tissue culture medium. Colonies demonstrating undifferentiated morphology are individually selected by micropipette, mechanically dissociated into clumps, and re-plated. Resulting ES cells are then routinely split every 4-7 days. For further details on methods of preparation human ES cells, see Reubinoff et al. Nat Biotechnol 2000, May: 18(5): 559; Thomson et al., [U.S. Pat. No. 5,843,780; Science 282: 1145, 1998; Curr. Top. Dev. Biol. 38: 133, 1998; Proc. Natl. Acad. Sci. USA 92: 7844, 1995]; Bongso et al., [Hum Reprod 4: 706, 1989]; and Gardner et al., [Fertil. Steril. 69: 84, 1998].

In addition, ES cells can be obtained from other species, including mouse (Mills and Bradley, 2001), golden hamster [Doetschman et al., 1988, Dev Biol. 127: 224-7], rat [Iannaccone et al., 1994, Dev Biol. 163: 288-92], rabbit [Giles et al. 1993, Mol Reprod Dev. 36: 130-8; Graves & Moreadith, 1993, Mol Reprod Dev. 1993, 30 36: 424-33], several domestic animal species [Notarianni et al., 1991, J Reprod Fertil Suppl. 43: 255-60; Wheeler 1994, Reprod Fertil Dev. 6: 563-8; Mitalipova et al., 2001, Cloning. 3: 59-67] and non-human primate species (Rhesus monkey and marmoset) [Thomson et al., 1995, Proc Natl Acad Sci U S A. 92: 7844-8; Thomson et al., 1996, Biol Reprod. 55: 254-9].

Extended blastocyst cells (EBCs) can be obtained from a blastocyst of at least nine days post fertilization at a stage prior to gastrulation. Prior to culturing the blastocyst, the zona pellucida is digested [for example by Tyrode's acidic solution (Sigma Aldrich, St Louis, MO, USA)] so as to expose the inner cell mass. The blastocysts are then cultured as whole embryos for at least nine and no more than fourteen days post fertilization (i.e., prior to the gastrulation event) in vitro using standard embryonic stem cell culturing methods.

Another method for preparing ES cells is described in Chung et al., Cell Stem Cell, Volume 2, Issue 2, 113-117, 7 Feb. 2008. This method comprises removing a single cell from an embryo during an in vitro fertilization process. The embryo is not destroyed in this process.

EG (embryonic germ) cells are prepared from the primordial germ cells obtained from fetuses of about 8-11 weeks of gestation (in the case of a human fetus) using laboratory techniques known to anyone skilled in the arts. The genital ridges are dissociated and cut into small portions which are thereafter disaggregated into cells by mechanical dissociation. The EG cells are then grown in tissue culture flasks with the appropriate medium. The cells are cultured with daily replacement of medium until a cell morphology consistent with EG cells is observed, typically after 7-30 days or 1-4 passages. For additional details on methods of preparation human EG cells see Shamblott et al., [Proc. Natl. Acad. Sci. USA 95: 13726, 1998] and U.S. Pat. No. 6,090, 622.

Yet another method for preparing ES cells is by parthenogenesis. The embryo is also not destroyed in the process.

The cells may be expanded in suspension, with or without a microcarrier, or in a monolayer. The expansion of the mixed population of cells in monolayer cultures or in suspension culture may be modified to large scale expansion in bioreactors or multi/hyper stacks by methods well known to those versed in the art.

According to some embodiments, the expansion phase is effected for at least one to 20 weeks, for example at least one week, at least 2 weeks, at least 3 weeks, at least 4 weeks, at least 5 weeks, at least 6 weeks, at least 7 weeks, at least 8 weeks, at least 9 weeks or even 10 weeks. In embodiments, the expansion phase is effected for 1 week to 10 weeks, such 2 weeks to 10 weeks, 3 weeks to 10 weeks, 4 weeks to 10 weeks, or 4 weeks to 8 weeks. The time period may be any value or subrange within the recited ranges, including endpoints.

According to still other embodiments, the mixed population of cells are passaged at least one time during the expansion phase, at least twice during the expansion phase, at least three times during the expansion phase, at least four times during the expansion phase, at least five times during the expansion phase, at least six times during the expansion phase, or at least seven times during the expansion phase.

When cells are collected enzymatically, it is possible to continue the expansion for more than 8 passages, more than 9 passages and even more than 10 passages (e.g. 11-15 passages). The number of total cell doublings can be increased to greater than 30, e.g. 31, 32, 33, 34 or more. (See international patent application publication number WO 2017/021973, incorporated herein by reference in its entirety).

An extracellular matrix (ECM) is a three-dimensional network consisting of extracellular macromolecules and minerals, such as collagen, enzymes, glycoproteins and hydroxyapatite that provide structural and biochemical support to surrounding cells. Because multicellularity evolved independently in different multicellular lineages, the composition of ECM varies between multicellular structures; however, cell adhesion, cell-to-cell communication and differentiation are common functions of the ECM.

The animal extracellular matrix includes the interstitial matrix and the basement membrane. Interstitial matrix is present between various animal cells (i.e., in the intercellular spaces). Gels of polysaccharides and fibrous proteins fill the interstitial space and act as a compression buffer against the stress placed on the ECM. Basement membranes are sheet-like depositions of ECM on which various epithelial cells rest. Each type of connective tissue in animals has a type of ECM: collagen fibers and bone mineral comprise the ECM of bone tissue; reticular fibers and ground substance comprise the ECM of loose connective tissue; and blood plasma is the ECM of blood.

Suitable extracellular matrix components for use within the scope of the present disclosure may include, but are not necessarily limited to, matrigel, vitronectin, gelatin, collagen I, collagen IV, laminin (e g laminin 521), fibronectin poly-D-lysine, their derivatives, or a combination thereof. In specific embodiments, the human laminin is human laminin 511 E8 fragment.

In some embodiments, the microcarriers may comprise one or more of polystyrene, cross-linked dextran, magnetic particles, microchips, cellulose, hydroxylated methacrylate, collagen, gelatin, polystyrene, plastic, glass, ceramic, or silicone. In some embodiments, the microcarriers are composed of polystyrene, surface-modified polystyrene, chemically modified polystyrene, cross-linked dextran, cellulose, acrylamide, collagen, alginate, gelatin, glass, DEAE-dextran, or a combination thereof. In some embodiments, the microcarrier is composed of polystyrene. In some embodiments, the microcarrier is composed of surface-modified polystyrene. In some embodiments, the microcarrier is composed of chemically modified polystyrene. In some embodiments, the microcarrier is composed of cross-linked dextran. In some embodiments, the microcarrier is composed of cellulose. In some embodiments, the microcarrier is composed of acrylamide. In some embodiments, the microcarrier is composed of collagen. In some embodiments, the microcarrier is composed of alginate. In some embodiments, the microcarrier is composed of gelatin. In some embodiments, the microcarrier is composed of glass. In some embodiments, the microcarrier is composed of DEAE-dextran. In some embodiments, the microcarriers are not coated.

In some embodiments, the microcarriers are coated. In embodiments, the microcarriers may be coated with matrigel, laminin, vitronectin, collagen, their derivatives, or a combination thereof. In embodiments, the microcarriers may be coated by poly-lysine, poly-L-lysine, poly-D-lysine, fibronectin, tenascin, dextran, a peptide, or a combination thereof. In some embodiments, the microcarrier is coated with laminin. In some embodiments, the microcarrier is coated with Matrigel. In some embodiments, the microcarrier is coated with collagen. In some embodiments, the s microcarrier is coated with poly-lysine. In some embodiments, the microcarrier is coated with poly-L-lysine. In some embodiments, the microcarrier is coated with poly-D-lysine. In some embodiments, the microcarrier is coated with vitronectin. In some embodiments, the microcarrier is coated with fibronectin. In some embodiments, the microcarrier is coated with tenascin. In some embodiments, the microcarrier is coated with dextran. In some embodiments, the microcarrier is coated with a peptide.

In some embodiments, the microcarriers may be spherical, smooth, macroporous, rod-shaped, or a combination thereof. In some embodiments, the microcarriers may be coupled with protamine or polylysine. In some embodiments, the microcarrier is spherical. In some embodiments, the s microcarrier is ellipsoidal. In some embodiments, the microcarrier is rod-shaped. In some embodiments, the microcarrier is disc-shaped. In some embodiments, the microcarrier is porous. In some embodiments, the microcarrier is non-porous. In some embodiments, the microcarrier is smooth. In some embodiments, the microcarrier is flat.

In some embodiments, the microcarriers are neutral. In some embodiments, the microcarriers are negatively charged. In some embodiments, the microcarriers are hydrophilic.

In some embodiments, the microcarriers may have a surface area of 25 cm$^2$, 50 cm$^2$, 75 cm$^2$, 100 cm$^2$, 125 cm$^2$, 150 cm$^2$, 175 cm$^2$, 200 cm$^2$, 225 cm$^2$, 250 cm$^2$, 500 cm$^2$, 625 cm$^2$, 750 cm$^2$, 1,000 cm$^2$, 1,250 cm$^2$, 5,000 cm$^2$, or 7,500 cm$^2$. The surface area may be any value or subrange within the recited ranges, including endpoints.

In specific embodiments, the microcarriers are surface treated to enhance cell attachment, maximizing cell yield and viability. The microcarriers may be comprised of USP Class VI polystyrene material, which provides a consistent platform. In some embodiments, the microcarriers create a synthetic surface on the microcarriers for stem cell expansion. An enhanced attachment surface treatment infuses the surface of the microcarriers with oxygen to improve cell attachment. In some embodiments, the microcarriers are nonpyrogenic. In some embodiments, the microcarriers are optimized for mesenchymal stem cell applications. In specific embodiments, the beads may vary in size from 125-212 μm. In specific embodiments, the density of the microcarriers may be 1.026±0.004. In specific embodiments, the microcarriers may be 360 cm$^2$/gram.

In some embodiments, the method comprises combining the hESCs with laminin or a derivative thereof to improve the cell attachment to the carrier surface. In specific embodiments, the laminin is human laminin 511. As alternative embodiments, several other extracellular matrices may be used for cell attachment, such as including, but not necessarily limited to, vitronectin, fibronectin, collagen, matrigel, or derivatives thereof.

In some embodiments, the cells may be cultured for one day, two days, three days, four days, five days, six days, seven days, eight days, nine days, ten days, eleven days, twelve days, thirteen days, or fourteen days.

In some embodiments, the cells may be cultured in a working volume of between 10 mL and 3,000 mL, for example about 10 mL, 20 mL, 30 mL, 40 mL, 50 mL, 100 mL, 250 mL, 500 mL, 750 mL, 1,000 mL, or 3,000 mL. The volume may be any value or subrange within the recited ranges, including endpoints.

In some embodiments, the cultured cells may be expanded further.

In some embodiments, the cultured cells may remain undifferentiated. Undifferentiated cells may be identified by expression of various markers, such as including, but not necessarily limited to, SSEA-5, TRA-1-60, Oct-4, and Nanog. In some embodiments, undifferentiated cells express SSEA-5. In some embodiments, undifferentiated cells express TRA-1-60. In some embodiments, undifferentiated cells express Oct-4. In some embodiments, undifferentiated cells express Nanog. In some embodiments, undifferentiated cells express both SSEA-5 and TRA-1-60. In some embodiments, undifferentiated cells express both Oct-4 and Nanog. In some embodiments, undifferentiated cells express SSEA-5, TRA-1-60, Oct-4, and Nanog.

In some embodiments, the cells may be cultured in a feeder cell-conditioned medium. ES culturing methods may include the use of feeder cell layers which secrete factors needed for stem cell proliferation, while at the same time, inhibiting their differentiation. The culturing is typically effected on a solid surface, for example a surface coated with gelatin or vimentin. Exemplary feeder layers include human embryonic fibroblasts, adult fallopian epithelial cells, primary mouse embryonic fibroblasts (PMEF), mouse embryonic fibroblasts (MEF), murine fetal fibroblasts (MFF), human embryonic fibroblast (HEF), human fibroblasts obtained from the differentiation of human embryonic stem cells, human fetal muscle cells (HFM),human fetal skin cells (HFS), human adult skin cells, human foreskin fibroblasts (HFF), human umbilical cord fibroblasts, human cells obtained from the umbilical cord or placenta, and human marrow stromal cells (hMSCs). Growth factors may be added to the medium to maintain the ESCs in an undifferentiated state. Such growth factors include bFGF and/or TGF. In another embodiment, agents may be added to the medium to maintain the hESCs in a naive undifferentiated state—see for example Kalkan et al., 2014, Phil. Trans. R. Soc. B, 369: 20130540.

hESCs are typically plated on top of the feeder cells 1-4 days later in a supportive medium (e.g. NUTRISTEM® or NUT(+) with human serum albumin,). Additional factors may be added to the medium to prevent differentiation of the ESCs such as bFGF and TGFI3. Once a sufficient amount of hESCs is obtained, the cells may be mechanically disrupted (e.g. by using a sterile tip or a disposable sterile stem cell tool; 14602 Swemed). Alternatively, the cells may be removed by enzymatic treatment (e.g. collagenase A, or TrypLE Select). This process may be repeated several times to reach the necessary amount of hESC. According to some embodiments, following the first round of expansion, the hESCs are removed using TrypLE Select and following the second round of expansion, the hESCs are removed using collagenase A.

Feeder cell free systems have also been used in ES cell culturing, such systems utilize matrices supplemented with serum replacement, cytokines and growth factors (including IL6 and soluble IL6 receptor chimera) as a replacement for the feeder cell layer. Stem cells can be grown on a solid surface such as an extracellular matrix (e.g., MATRIGELR™, laminin or vitronectin) in the presence of a culture medium—for example the Lonza L7 system, mTeSR, StemPro, XFKSR, E8, NUTRISTEM®). Unlike feeder-based cultures which require the simultaneous growth of feeder cells and stem cells and which may result in mixed cell populations, stem cells grown on feeder-free systems are easily separated from the surface. The culture medium used for growing the stem cells contains factors that effectively inhibit differentiation and promote their growth such as MEF-conditioned medium and bFGF.

Also within the scope of the present disclosure are methods for expanding and maintaining human embryonic stem cells (hESCs) in an undifferentiated state, comprising culturing human pluripotent stem cells on a non-adherent surface to obtain a population of undifferentiated hESCs, combining said population of undifferentiated hESCs with microcarriers in growth media, and expanding said population of cells.

Examples of non-adherent cell culture plates include those manufactured by Nunc (e.g. Hydrocell Cat No. 174912), etc. In other embodiments, non-adherent suspension culture dishes may be used (e.g., Corning).

According to some embodiments, when the cells are cultured on the non-adherent substrate, e.g. cell culture plates, the atmospheric oxygen conditions are 20%. However, manipulation of the atmospheric oxygen conditions is also contemplated such that the atmospheric oxygen percent is less than about 20%, 15%, 10%, 9%, 8%, 7%, 6% or even less than about 5% (e.g. between 1% -20%, 1%-10% or 0-5%). According to other embodiments, the cells are cultured on the non-adherent substrate initially under normal atmospheric oxygen conditions and then lowered to less than normal atmospheric oxygen conditions.

In some embodiments, the method may further comprise freezing (e.g., cryopreserving) the expanded population of cells. Examples of media suitable for cryopreservation include but are not limited to 90% Human Serum/10% DMSO, Media 3 10% (CS10), Media 2 5% (CS5) and Media 1 2% (CS2), Stem Cell Banker, PRIME XV° FREEZIS, HYPOTHERMASOL®, Trehalose, etc.

In further embodiments, the cryopreservation medium includes: a purine nucleoside (e.g., adenosine), a branched glucan (e.g., dextran 40), a zwitterionic organic chemical buffering agent (e.g., HEPES (N-(2-Hydroxyethyl) pipera-zine EN'-(2E ethanesulfonic acid))), and a cell tolerable polar aprotic solvent (e.g., dimethyl sulfoxide (DMSO)). In still further embodiments, one or more of the purine nucleo-side, branched glucan, buffering agent, and the polar aprotic solvent are generally recognized as safe by the US FDA.

In some embodiments, the cryopreservation media further includes one or more of: a sugar acid (e.g., lactobionic acid), one or more of a base (e.g., sodium hydroxide, potassium hydroxide), an antioxidant (e.g., L-glutathione), one or more halide salt (e.g., potassium chloride, sodium chloride, mag-nesium chloride), a basic salt (e.g., potassium bicarbonate), phosphate salt (e.g., potassium phosphate, sodium phos-phate, potassium phosphate), one or more sugars (e.g., dextrose, sucrose), sugar alcohol, (e.g., mannitol), and water.

In other embodiments, one or more of the sugar acid, base, halide salt, basic salt, antioxidant, phosphate salt, sugars, sugar alcohols are generally recognized as safe by the US FDA.

DMSO can be used as a cryoprotective agent to prevent the formation of ice crystals, which can kill cells during the cryopreservation process. In some embodiments, the cryo-preservable medium comprises between about 0.1% and about 2% DMSO (v/v). In some embodiments, the cryopre-servable medium comprises between about 1% and about 20% DMSO. In some embodiments, the cryopreservable medium comprises about 2% DMSO. In some embodi-ments, the cryopreservable medium comprises about 5% DMSO.

In some embodiments, the method may further comprise culturing the expanded population of cells on an adherent surface in a medium comprising a differentiating agent to obtain differentiating cells. Examples of adherent substrates or a mixture of substances could include but are not limited to fibronectin, laminin, polyD-lysine, collagen and gelatin. In one embodiment, the differentiating is effected in the presence of nicotinamide (e.g. between 0.01-100 mM, 0.1-100 mM, 0.1-50 mM, 5-50 mM, 5-20 mM, e.g. 10 mM), and in the absence of activin A. The concentration may be any value or subrange within the recited ranges, including end-points.

According to some embodiments, the cells are cultured on the adherent substrate initially under normal atmospheric oxygen conditions and subsequently the oxygen is lowered to less than normal atmospheric oxygen conditions.

According to some embodiments, when the cells are cultured on the adherent substrate e.g. laminin, the atmo-spheric oxygen conditions are 20%. They may be manipu-lated such that the atmospheric oxygen percentage is less than about 20%, 15%, 10%, more preferably less than about 9%, less than about 8%, less than about 7%, less than about 6% and more preferably about 5% (e.g. between 1% - 20%, 1% -10% or 0-5%). The amount may be any value or subrange within the recited ranges, including endpoints.

In some embodiments, the cells are cultured in a feeder cell-conditioned medium, as described in detail above.

In some embodiments, the cells are cultured in the absence of feeder cells.

In some embodiments, after initial expansion, the cells may be further expanded.

In some embodiments, the cells may be cultured for one day, two days, three days, four days, five days, six days, or seven days.

In some embodiments, the cultured cells may be expanded further.

In some embodiments, the cultured cells of the suspend-able expansion complex are harvested and further differen-tiated. In some embodiments, the cultured cells of the suspendable expansion complex are further differentiated by changing the growth medium. In some embodiments, the cultured cells of the suspendable expansion complex remain undifferentiated and pluripotent.

ADDITIONAL EMBODIMENTS

The present disclosure provides the following illustrative embodiments.

Embodiment 1—A method for expanding and maintaining human embryonic stem cells (hESCs) in an undifferentiated, pluripotent state, the method comprising the steps of (a) simultaneously combining human embryonic stem cells, an extracellular matrix component (ECM), and a microcarrier in growth media to form a suspendable expansion complex, and (b) culturing the suspendable expansion complex for a period of time.

Embodiment 2—The method of embodiment 1, wherein the microcarriers comprise one or more of polystyrene, cross-linked dextran, magnetic particles, microchips, cellulose, hydroxylated methacrylate, collagen, gelatin, polystyrene, plastic, glass, ceramic, silicone, or a combination thereof.

Embodiment 3—The method of embodiment 1 or 2, wherein the microcarriers are spherical, smooth, macroporous, rod-shaped, or a combination thereof.

Embodiment 4—The method of any of embodiments 1 to 3, wherein the ECM comprises matrigel, laminin, vitronectin, collagen, their derivatives, or a combination thereof.

Embodiment 5—The method of embodiment 1, wherein the ECM is human laminin

Embodiment 6—The method of embodiment 5 wherein the human laminin is human laminin 511 E8 fragment.

Embodiment 7—The method of any of embodiments 1 to 3, wherein the microcarriers are not coated.

Embodiment 8—The method of any of embodiments 1 to 7, wherein the microcarriers are coupled with protamine or polylysine.

Embodiment 9—The method of any of embodiments 1 to 7, wherein the microcarriers are neutral or negatively charged.

Embodiment 10—The method of embodiment 9, wherein the microcarriers are neutral.

Embodiment 11—The method of embodiment 9, wherein the microcarriers are negatively charged.

Embodiment 12—The method of any of embodiments 1 to 11, wherein the microcarriers are hydrophilic.

Embodiment 13—The method of any of embodiments 1 to 12, wherein the suspendable expansion complex is cultured for at least about one day.

Embodiment 14—The method of embodiment 13, wherein the suspendable expansion complex is cultured from about one day to about fourteen days.

Embodiment 15—The method of embodiment 1, wherein the cultured cells of the suspendable expansion complex are harvested and expanded further by repeating steps (a) and (b).

Embodiment 16—The method of embodiment 1 wherein the cultured cells of the suspendable expansion complex are harvested and further differentiated.

Embodiment 17—The method of embodiment 16 wherein the cultured cells of the suspendable expansion complex are further differentiated by changing the growth medium.

Embodiment 18—The method of embodiment 1, wherein the cultured cells of the suspendable expansion complex remain undifferentiated and pluripotent.

Embodiment 19—The method of embodiment 16, wherein the undifferentiated cells express at least about 80% of each of SSEA-5 and TRA-1-60.

Embodiment 20—The method of embodiment 16, wherein the undifferentiated cells express at least about 70% of each of Oct-4 and Nanog.

Embodiment 21—The method of embodiment 16, wherein the undifferentiated cells express at least about 80% of SSEA-5, at least about 80% of TRA-1-60, at least about 70% of Oct-4, and at least about 70% of Nanog.

Compositions

In another aspect, provided herein are suspendable expansion complex compositions comprising human embryonic stem cells, an extracellular matrix component (ECM), and a microcarrier.

Human embryonic stem cells, extracellular matrices, and microcarriers are described in detail elsewhere herein.

Expansion complex ranges may vary. In the following tables, the range of the complex components are detailed in different units for the ECM component.

TABLE 1

| Expansion complex of MC ECM and cells (ECM in µg) | | | |
|---|---|---|---|
| | MCs | ECM - Laminin 511 E8 fragment (µg per cm$^2$) | hESCs (cells per cm$^2$) |
| Min | 1 cm$^2$ | 0.125 | 9,600 |
| Max | 1 cm$^2$ | 0.125 | 50,000 |

The ECM component can be presented by mol/cm$^2$ by using the laminin 511 E8 fragment's molecular weight (150 KDa).

TABLE 2

| Expansion complex of MC ECM and cells (ECM in mol) | | | |
|---|---|---|---|
| | MCs | ECM - Laminin 511 E8 fragment (mol per cm$^2$) | hESCs (cells per cm$^2$) |
| Min | 1 cm$^2$ | $8.33 \times 10^{-13}$ | 9,600 |
| Max | 1 cm$^2$ | $8.33 \times 10^{-13}$ | 50,000 |

The ECM component can also be presented by the number of molecules/cm$^2$ by using molecular weight (150 KDa) multiplied by Avogadro's number ($6.022 \times 10^{23}$).

TABLE 3

| Expansion complex of MC ECM media and cells (ECM molecules) | | | |
|---|---|---|---|
| | MCs | ECM - Laminin 511 E8 fragment (molecules per cm$^2$) | hESCs (cells per cm$^2$) |
| Min | 1 cm$^2$ | $5.01833 \times 10^{11}$ | 9,600 |
| Max | 1 cm$^2$ | $5.01833 \times 10^{11}$ | 50,000 |

In some embodiments, the following specification parameters may be expanded:

Of hESCs (cells)—4,000-600,000 cells per cm$^2$ of microcarriers

Laminin 511 E8 fragment (µg per cm$^2$ of microcarriers)—0.125 µg per cm$^2$ or higher.

In some embodiments, the composition may further comprise a growth medium. Non-limiting examples of commercially available basic media that may be utilized in accordance with this disclosure comprise NUTRISTEM®

(without bFGF and TGF for ESC differentiation, with bFGF and TGF for ESC expansion), NEUROBASAL™, KO-DMEM, DMEM, DMEM/F12, CELLGRO™ Stem Cell Growth Medium, or X-VIVO™. The basic medium may be supplemented with a variety of agents as known in the art dealing with cell cultures. The following is a non-limiting reference to various supplements that may be included in the culture to be used in accordance with the present disclosure: serum or with a serum replacement containing medium, such as, without being limited thereto, knock out serum replacement (KOSR), NUTRIDOMA-CS, TCH™, N2, N2 derivative, or B27 or a combination; an extracellular matrix (ECM) component, such as, without being limited thereto, fibronectin, laminin, collagen and gelatin. The ECM may then be used to carry the one or more members of the TGFI3 superfamily of growth factors; an antibacterial agent, such as, without being limited thereto, penicillin and streptomycin; and non-essential amino acids (NEAA), neurotrophins which are known to play a role in promoting the survival of SCs in culture, such as, without being limited thereto, BDNF, NT3, NT4.

As described above, the microcarriers may comprise one or more of polystyrene, cross-linked dextran, magnetic particles, microchips, cellulose, hydroxylated methacrylate, collagen, gelatin, polystyrene, plastic, glass, ceramic, silicone. In some embodiments, the microcarrier is composed of polystyrene. In some embodiments, the microcarrier is composed of surface-modified polystyrene. In some embodiments, the microcarrier is composed of chemically modified polystyrene. In some embodiments, the microcarrier is composed of cross-linked dextran. In some embodiments, the microcarrier is composed of cellulose. In some embodiments, the microcarrier is composed of acrylamide. In some embodiments, the microcarrier is composed of collagen. In some embodiments, the microcarrier is composed of alginate. In some embodiments, the microcarrier is composed of gelatin. In some embodiments, the microcarrier is composed of glass. In some embodiments, the microcarrier is composed of DEAE-dextran.

As described above, the microcarriers may be spherical, smooth, macroporous, rod-shaped, or a combination thereof.

In some embodiments, the microcarriers may be coated with matrigel, laminin, vitronectin, collagen, their derivatives, or a combination thereof. In some embodiments, the laminin is human laminin 511.

In some embodiments, the microcarriers are not coated.

In some embodiments, the microcarriers have a surface area of 25 cm² to 7,500 cm², e.g., about 25 cm², 50 cm², 75 cm², 100 cm², 125 cm², 150 cm², 175 cm², 200 cm², 225 cm², 250 cm², 500 cm², 625 cm², 750 cm², 1,000 cm², 1,250 cm², 5,000 cm², or 7,500 cm². The surface area may be any value or subrange within the recited ranges, including endpoints.

In some embodiments, the microcarriers are coupled with protamine or polylysine. In some embodiments, the microcarriers are neutral. In some embodiments, the microcarriers are negatively charged. In some embodiments, the microcarriers are hydrophilic.

It is understood that the examples and embodiments described herein are for illustrative purposes only and that various modifications or changes in light thereof will be suggested to persons skilled in the art and are to be included within the spirit and purview of this application and scope of the appended claims. All publications, patents, and patent applications cited herein are hereby incorporated by reference in their entirety for all purposes.

ADDITIONAL EMBODIMENTS

The present disclosure provides the following illustrative embodiments.

Embodiment 22—A suspendable expansion complex composition comprising human embryonic stem cells, an extracellular matrix component (ECM), and a microcarrier.

Embodiment 23—The composition of embodiment 22, further comprising a growth medium.

Embodiment 24—The composition of embodiment 22 or 23, wherein the microcarriers comprise one or more of polystyrene, cross-linked dextran, magnetic particles, microchips, cellulose, hydroxylated methacrylate, collagen, gelatin, polystyrene, plastic, glass, ceramic, silicone.

Embodiment 25—The composition of any of embodiments 22 to 24, wherein the microcarriers are spherical, smooth, macroporous, rod-shaped, or a combination thereof.

Embodiment 26—The composition of any of embodiments 22 to 25, wherein the microcarriers are coated with matrigel, laminin, vitronectin, collagen, their derivatives, or a combination thereof.

Embodiment 27—The composition of embodiment 26 wherein the laminin is human laminin Embodiment 28—The composition of embodiment 27, wherein the human laminin is human laminin 511 E8 fragment.

Embodiment 29—The composition of any of embodiments 22 to 28, wherein the microcarriers are not coated.

Embodiment 30—The composition of any of embodiments 22 to 29, wherein the microcarriers are coupled with protamine or polylysine.

Embodiment 31—The composition of any of embodiments 22 to 30, wherein the microcarriers are neutral or negatively charged.

Embodiment 32—The composition of embodiment 31, wherein the microcarriers are neutral.

Embodiment 33—The composition of embodiment 31, wherein the microcarriers are negatively charged.

Embodiment 34—The composition of any of embodiments 22 to 29, wherein the microcarriers are hydrophilic.

EXAMPLES

Example 1: Methods for hESC Expansion

Scale-up of hESC production is done on many growth platforms. From growing hESC cell suspension, or attached to 2D flasks such as roller bottles, cell factories or 3D hollow-fibers and macro-carriers such as BioNocII, and Fibra Cell discs.

Fully controlled and closed systems were used for simple mammalian cell growth for many years. Those systems allowed for the manufacturing of large industrial lots of antibodies and proteins. Most of these systems require cells that are inherently grown or were adapted to grow in suspension as single cells. Early attempts to expand hESCs in suspension were not successful as they formed aggregates that tended to lose their pluripotency and spontaneously differentiate. Adaptation to hESC grown as a single cell suspension most of the time compromised genetic stability and caused karyotype abnormalities. Recently such methodology was greatly improved (AMIT Michal, Itzkvitz Eldor Joseph Patent # EP2059586B1, U.S. Pat. No. 9,040, 297B2), their innovation is to grow hESCs without adherence to any kind of substrate or coating in serum-free, serum replacement-free, xeno-free, feeder-free and protein carrier-free. That was enabled in part by the addition of a soluble interleukin-6 receptor (sIL6R, >10 ng/ml), soluble interleukin-6 (IL6), leukemia inhibitor factor (LIF, 1000-3000 u/ml) as well as bFGF, TGFb1 and TGFb3.

Several studies have used microcarriers to grow hESCs cultures. Their properties of being suspended in solution, while providing them with surface for adherent cells to grow on, made them ideal for growing adherent cell culture in a closed and controlled environment. A potential benefit of using microcarriers for large-scale production is that the surface-area-to-volume ratio is greatly increased over traditional static culture processes, so cell density may be increased, and the required footprint reduced.

Many different types of microcarriers (MCs) are commercially available. MCs can be made from polystyrene such as HyQSphere (HyClone) and Hillex (SoloHill Engineering) brands or made from cross-linked dextran such as the Cytodex brand (GE Healthcare). Although most microcarriers are spherical and smooth, others have macroporous surfaces such as Cytopore brand (GE) and alternatives such as rod-shaped carriers such as DE-53 (Whatman). Additional technological advances include infusion of magnetic particles into the MC that may help in cell separation from beads (GEM particles from Global Cell Solutions) and chip-based microcarriers such as the μHex product (Nunc) that provide a traditional flat surface for cell growth while maintaining the high surface to volume ratio of traditional microcarriers. Selecting a microcarrier for cell expansion is not a trivial task. Different properties of microcarriers may significantly affect expansion rates, cell pluripotency, ability to perform (in the case of hESCs its ability to differentiate into different lineages), genetic stability, etc. Some surface chemistry modifications can improve cell adhesion. Such methods include applying positive or negative charges and optional coating with extracellular matrix proteins (Lam 2015 BioResearch Open Access Volume 4.1, Cherian 2020 Frontiers in Pharmacology Volume 11 Article 654).

First attempts to grow embryonic stem cells (ESC) on microcarriers in stirred suspension were published in 2005-2007 (Fok et al Stem Cells 2005; 23:1333-1342, Abranches et al Biotechnol. Bioeng. 96 (2007), pp. 1211-1221, and Stefanie Terstegge & Oliver Brustle US20070264713A1). Expansion and passaging of hESC onto MC was demonstrated in 2009 using Cytodex 1, 3 and Solohil Plastic, Plastic plus and Hillex II (Nelson, Janssen Biotech Inc, US20180265842A1, U.S. Pat. No. 9,969,972B2) including their differentiation to definitive endoderm and pancreatic cells on MCs, or cardiomyocytes (Oh et al. EP2479260B1). Most of the developed processes included the coating of MCs with Matrigel, in some cases Laminin, or Vitronectin was used as coating of MC precoated with collagen. One study performed the hESC expansion in a controlled environment using the Synthemax® II coated MC (Corning, Silva 2015). The main conditions and results of these studies are summarized in Table 4. Those studies did not yet advance to large vessels, but in general they established comparable results to standard practice in static flasks. But the next step toward large scale production in controlled environment is yet to be made prior to the present disclosure.

TABLE 4

| Known hESC and iPSC scale up studies using microcarriers. | | | | | | |
|---|---|---|---|---|---|---|
| hPSC line | Vessel type | Working volume | MC Type | Culture media | Fold/days | Max cell density |
| H1, H9 | Spinner Flask | 50 ml | MG coated Hyclone MC | DMEM-F12 | 45/8 days | 0.9M/ml |
| ESI-17 | Spinner Flask | 80 ml | SoloHill-Hillex II MC uncoated | KO-SR DMEM | 6/5 days | 0.37M/ml |
| H1, H9 | NA-6 wells | 100 ml | MG coated Cytodex 3 | DMEM-F12 | 3.3/3.5 days | 3.3M/ml |
| HES-2, HES-3 | Spinner Flask | 50 ml | Rod shape cellulose MC | MEF-CM | 17.5/5 days | 3.5M/ml |
| H1, B12-3 | Spinner Flask | 45 ml | MG coated Hyclone MC | Essential 8 | 10/8 days | 0.5M/ml |
| SHEF3 hESCs | Techne glass | 30 ml | Cultispher-S (gelatin based) uncoated | KO-SR DMEM | 10/7 days | 1M/ml |
| HES2/3, IMR90 | Spinner Flask | 50 ml | MG coated DE53 | Essential 8 mTeSR1 | 5/7 days | 2.4M/ml |
| HES2/3 | 2D shaker | 5 ml | 10 types, MG/mLN coated | MEF CM | 4-8/7 days | 1.4M/ml |
| H9, IMR90 | Spinner Flask | 50 ml | Solohil VT/MG coated | TeSR2 or mTeSR1 | 25/6 days | 1.9M/ml |
| HES3, IMR90 | 2D shaker | 4 ml | MG coated DE53 | mTeSR1 | 20/7 days | 6.1M/ml |
| HES3, IMR90 | Spinner/ Rocker | 25 ml | Cytodex 1, MG coated | mTeSR1 | 7.5/7 days | 3M/ml |
| SA181 | Cellferm-pro 180 ml BR | 60 ml | Synthemax II PS MC | DEF-CS basal medium | 5/7 days | 1M/ml |

TABLE 4-continued

Known hESC and iPSC scale up studies using microcarriers.

| | | | | | | | |
|---|---|---|---|---|---|---|---|
| H9 | Spinner Flask | 50 ml | Solohil P, FC coated with vitronectin | Essential 8 | | 5/6 days | 0.45M/ml |
| HES3 IMR90, | Orbital shaker, spinner | 5 ml, 50 ml | Solohil P, P+, GE PS | mTeSR1 | | 18/7 days | 3.5M/ml |

| hPSC line | Max cells/vessel | Parameter improved | Ref. | Pat# |
|---|---|---|---|---|
| H1, H9 | 45M | seeding density (clamps) | Lock | |
| ESI-17 | 30M | Single cell seeding | Philips 2008 | US20160024467A1 |
| H1, H9 | 6.6M | hESC/MC ICB, MG coating | Nei 2009 | U.S. Pat. No. 10,487,312B2 |
| HES-2, HES-3 | 175M | Shape and MG coating | Oh 2009 | EP2479260B1 U.S. Pat. No. 8,828,720B2 |
| H1, B12-3 | 27M | Effect of variables discussed | Kehoe 2010 | |
| SHEF3 hESCs | 30M | Rock inhibitor (RI), single cells | Storm 2010 | |
| HES2/3, IMR90 | 60M | Feeding, protective polymers to reduce shear | Leung 2011 | EP2479260B1 U.S. Pat. No. 8,828,720B2 U.S. Pat. No. 8,716,018B2 |
| HES2/3 | 11.2M | MG coating, charge effect | Chen 2011 | EP2479260B1 U.S. Pat. No. 8,828,720B2 |
| H9, IMR90 | 95M | RI, various coating | Fan 2013 | |
| HES3, IMR90 | 24.4M | Feeding 2/day, NPC Diff. | Bardy 2013 | EP2479260B1 U.S. Pat. No. 8,828,720B2 U.S. Pat. No. 8,716,018B2 |
| HES3, IMR90 | 75M | Cardiomyocytes diff. | Ting 2014 | EP2479260B1 U.S. Pat. No. 8,828,720B2 |
| SA181 | 60M | Feeder free defined media, controlled growth | Silva 2015 | U.S. Pat. No. 8,716,018B2 |
| H9 | 22.5M | Full protocols enclosed | Ashok 2016 | |
| HES3 IMR90, | 175M | Charge effect with and without PLL, with mouse LN111 or human LN521 | Lam 2015 | EP2479260B1 U.S. Pat. No. 8,828,720B2 U.S. Pat. No. 8,716,018B2 |

GMP grade feeder free and serum free hESCs banks were previously generated from clinically approved hESCs lines (HADC102, H1). Here, hESCs were propagated for several passages on uncoated flasks by adding the iMatrix-511-E8 (No. 2009-234583/PCTJP2010-067618/WO2011-043405, Miyazaki et al. 2012 Nat Commun. 2012 Dec. 4; 3: 1236) synthetic fragment to the seeding solution. This methodology was used for a scale-up of hESC culturing on MCs for development of a scale up process. In a proof of concept study, hESCs (H1) were cultured on non-adherent T25 flasks in mTeSR plus media supplemented with iMatrix-511-E8—0.125 μgr/cm$^2$ using Synthemax® II or Enhanced Attachment (Corning) MC.

The combination of human laminin 511 as a coating, specifically iMatrix-511-E8 (synthetic fraction of laminin 511), with those specific two MCs (others were tested in the POC study and failed) in suspension, to allow for expansion of hESCs in a culturing system, allows for scale up. Human laminin 511, specifically iMatrix E8, was used here for the first time for coating MCs in a scaled up system. Former publications teach about culturing hESCs on laminin coated tissue culture, or about hESC culturing on different MCs with a variety of substrates covering in general all protein matrices (Matrigel, collagen, gelatin, vitronectin, laminin, or their derivatives or combinations).

This combination, as detailed above, makes the transfer to large scale much easier and linear when intending to use single-use bioreactors for hESC expansion.

As an additional point, the coating procedure was done using the high specificity of iMatrix 511 E8 to hESCs, it was used not as an agent for pre-coating the substrate before cell seeding, rather, by simplifying the process and adding this agent directly to the cell suspension before contact with the MCs. Thus, when cells are seeded, the MCs are not pre-coated, but having the iMatrix 511 E8 in the seeding solution enhances their specific attachment to those specific MCs.

Under current standard practices, microcarriers are coated before cell inoculation. The duration of the pre-coating step is highly variable, from 4 hrs at 37° C. to one month at 4° C., and it is difficult to control the coating procedure to be even upon all the surfaces, as MCs get compact in long static incubation and some of the surface is less accessible to coating as it is in contact with neighboring beads. A complete removal of the coating solution is needed before the equilibration step to the MCs in the growth media before MC equilibration and cell inoculation. The coating removal step is risky due to the sensitivity of the laminin coating to low humidity. If the laminin gets dry, it changes its adhesive properties. In a scaled-up system, with large volumes, this step is critical as it may not only affect the number of seeded cells; it can change the cell properties.

The innovation of the present disclosure over hESC expansion systems and techniques heretofore described is the combination or inoculation of ingredients in a single step which allows for a convenient inoculation of the hESC scaled-up system. In particular, the systems and methods described herein include the single step seeding step as described above, namely, (a) simultaneously combining human embryonic stem cells, an extracellular matrix component (ECM), and a microcarrier in growth media to form a suspendable expansion complex, and (b) culturing the suspendable expansion complex for a period of time. For example, by mixing all relevant materials together for inoculating the scaled-up system (the specific MC type, iMatrix511 E8 with cells), with no need to do pre-coating and then another step of seeding. That also includes the expansion of hESCs in a closed and controlled environment under GMP conditions. The specific combination of those materials for the scaled-up system, allows for easy and safe GMP translation.

Results

Seeding was done for 2 hrs. at 20,000 cells/cm$^2$ on Synthemax® II or Enhanced Attachment (Corning) MC in a non-treated T25 (Corning). At the end of the seeding step, 8 ml of mTeSR plus was added. 80% of the media was replaced every 24 hours and lactate levels and cell morphology (FIG. 1 and Table 6) were monitored. Harvesting was done on the 4$^{th}$ day after seeding using TrypLE Select. Cells were filtered through a 70 μm strainer to remove the MCs. Cells were cryopreserved in CS10. Pluripotency of thawed cells was assessed (Table 5, SSEA-5/TRA-1-60, Oct4/Nanog) after follow-up passage (P2) on TC treated flasks.

The results of the study as summarized in Table 6 indicate that efficient hESC expansion on MCs was achieved without reducing cell pluripotency (SSEA-5/TRA-1-60>98%, % Oct-4/Nanog>84%) and self-renewal (population doublings (PDL) in P1 ~4, P2 ~3) for both MC types.

TABLE 5

Pluripotency of hESCs grown for 1 passage on MC.

| Group | % SSEA-5/TRA-1-60 positive | % Oct-4/Nanog positive | Assay # |
|---|---|---|---|
| A Synthemax ® II | %98.62 | %84.26 | O-QCT-20-088 |
| B Enhanced Attachment | %98.34 | %84.92 | O-QCT-20-088 |

TABLE 6

Summary of passaging data for the experiments described herein.
Passaging data

| Group | Originated from | Dissociation reagent before seeding | P1 Passage duration (days) | P1 Lactate at passaging (mM) | P1 Seeding density (cells/cm$^2$) | P1 Harvesting density (cells/cm$^2$) | Yield | PDL | PDL/day | P2 Passage duration (days) | P2 Lactate at passaging (mM) |
|---|---|---|---|---|---|---|---|---|---|---|---|
| A Synthemax ® II | DEVOPC-PRO-04, GRP# 3B | ReLeSR | 4 | 14.3 | 20,000 | 341,300 | 17.07 | 4.1 | 1.0 | 5 | 13.96 |
| B Enhanced Attachment | | | 4 | 13.71 | 20,000 | 317,100 | 15.86 | 4.0 | 1.0 | 5 | 11.70 |

| Group | Originated from | Dissociation reagent before seeding | P2 Seeding density (cells/cm$^2$) | P2 Harvesting density (cells/cm$^2$) | Yield | PDL | PDL/day | Total Yield | Total PDL | Total PDL/day |
|---|---|---|---|---|---|---|---|---|---|---|
| A Synthemax ® II | DEVOPC-PRO-04, | ReLeSR | 40,000 | 436,800 | 10.92 | 3.4 | 0.7 | 186 | 7.5 | 0.8 |

TABLE 6-continued

| | | Summary of passaging data for the experiments described herein. Passaging data | | | | | | | |
|---|---|---|---|---|---|---|---|---|---|
| B Enhanced Attachment | GRP# 3B | 40,000 | 264,000 | 6.60 | 2.7 | 0.5 | 105 | 6.7 | 0.7 |

Example 2: Manufacturing Capability and Scale-Up Plan

A fully integrated team would include PD, QC, QA, and manufacturing. World experts in PSC technology guided the differentiation of cells to specific functional lineages. There would be an experienced team for process development, formulation and large-scale production in bioreactors using microcarriers. In-house specialized cGMP production capabilities include 1) two independent clean rooms; 2) bioreactor cell production (currently 5 billion cells per batch); and 3) fill/finish capabilities.

Example 3: System for Scaling Up hESC Expansion

As described above, the combination of ingredients in a single step allows for the convenient inoculation of the hESC scaled-up system in accordance with the teachings of the present disclosure. Under the current standard practice, microcarriers are coated before cell inoculation. The duration of the pre-coating step is highly variable, from 4 hrs at 37° C. to a month at 4° C., and it is difficult to control the coating procedure to be even upon all the surfaces, as MCs get compact in long static incubation and some of the surface is less accessible to coating as it is in contact with neighboring beads. A complete removal of the coating solution is needed before the equilibration step to the MC in the growth media before MC equilibration and cell inoculation. The coating removal step is risky due to the sensitivity of the laminin coating to low humidity. If the laminin gets dry it changes its adhesive properties. In a scale-up system, with large volumes, this step is critical as it may not only affect the number of seeded cells, but it can also change the cells' properties.

The innovation of the present disclosure includes the seeding step as mentioned above, mixing all relevant materials together for inoculating the scaled-up system (the specific MC type, iMatrix-511 E8 with cells), with no need for pre-coating and an additional step of seeding. That also includes the expansion of hESCs in a closed and controlled environment under GMP conditions. The specific combination of these materials for the scale-up system, enables easy and safe GMP translation.

The process presented here (FIG. 3), involves thawing and expansion of hESCs as a traditional feeder-free 2D culture. Then hESCs are harvested and seeded directly in the hESCs expansion scaled-up system on MCs with iMatrix-511 E8 supplemented to the medium. At the end of hESCs expansion in the scaled-up system, the harvested cells can be cryopreserved as a hESC pluripotent bank for further expansion and/or continue directly to initiate differentiation.

For evaluation of cell growth, several parameters can be evaluated—

1) Lactate measurements—increase in lactate concentration in media along culturing is linear to # of live cells during hESC culturing.

2) Morphological assessment—Clumps of beads observed during hESC expansion in the scale-up system reflect cell growth in culture.

3) Passaging parameters—harvesting density (live cells/cm$^2$) of cells in addition to yield $$\left( \frac{\text{\# of cells harvested}}{\text{\# of cells seeded}} \right)$$

parameters.

Other hESC characterization methods were used to evaluate the harvested cells from the hESC expansion scale-up system—

1) Pluripotency markers expression—cryopreserved harvested cells from the hESCs expansion scale-up system culturing were stained for four well-known pluripotency markers (SSEA-5/TRA-1-60, Oct-4/Nanog) and analyzed by flow cytometry. High expression of these markers affirmed the identity and pluripotency state of the harvested cells from the hESC scale-up culturing system.

2) Karyotype analysis—during development runs, cells were cultured after harvesting from the hESCs scale-up culturing system and fixed. The cell karyotype was tested by the Giemsa banding method to ensure genetic stability.

Culturing of hESCs on Several Types of MCs hESCs were harvested from T-flasks and seeded in one inoculation step on several types of MCs with iMatrix-511 E8 supplemented to seeding medium. Cells were cultured for 4 days passage in the hESCs scale-up system. The MC types evaluated in the hESC expansion scale-up system are detailed in the Table 7. In addition, culturing hESCs on other types of micro and macro carriers (Pall Solohill Star-Plus, Pall Solohill Hillex®II, Pall Solohill Plastic, Pall Solohill Plastic Plus, ESCO BioNOC II, CelliGen Fibracell Disks, Advanced Biometrix SphereCol®Type I Collagen Coated Beads, Cytodex® 3) was tested (data not shown). These micro and macro carriers were not continued after a first screening of MCs.

TABLE 7

| MCs tested in the hESCs expansion scale-up system. | | |
|---|---|---|
| Group # | MCs | iMatrix-511-E8 concentration (ug/cm$^2$) |
| 1.1 | Corning Synthemax ® II | 0.125 |
| 1.2 | Corning Enhanced Attachment | 0.125 |

Figure 4:
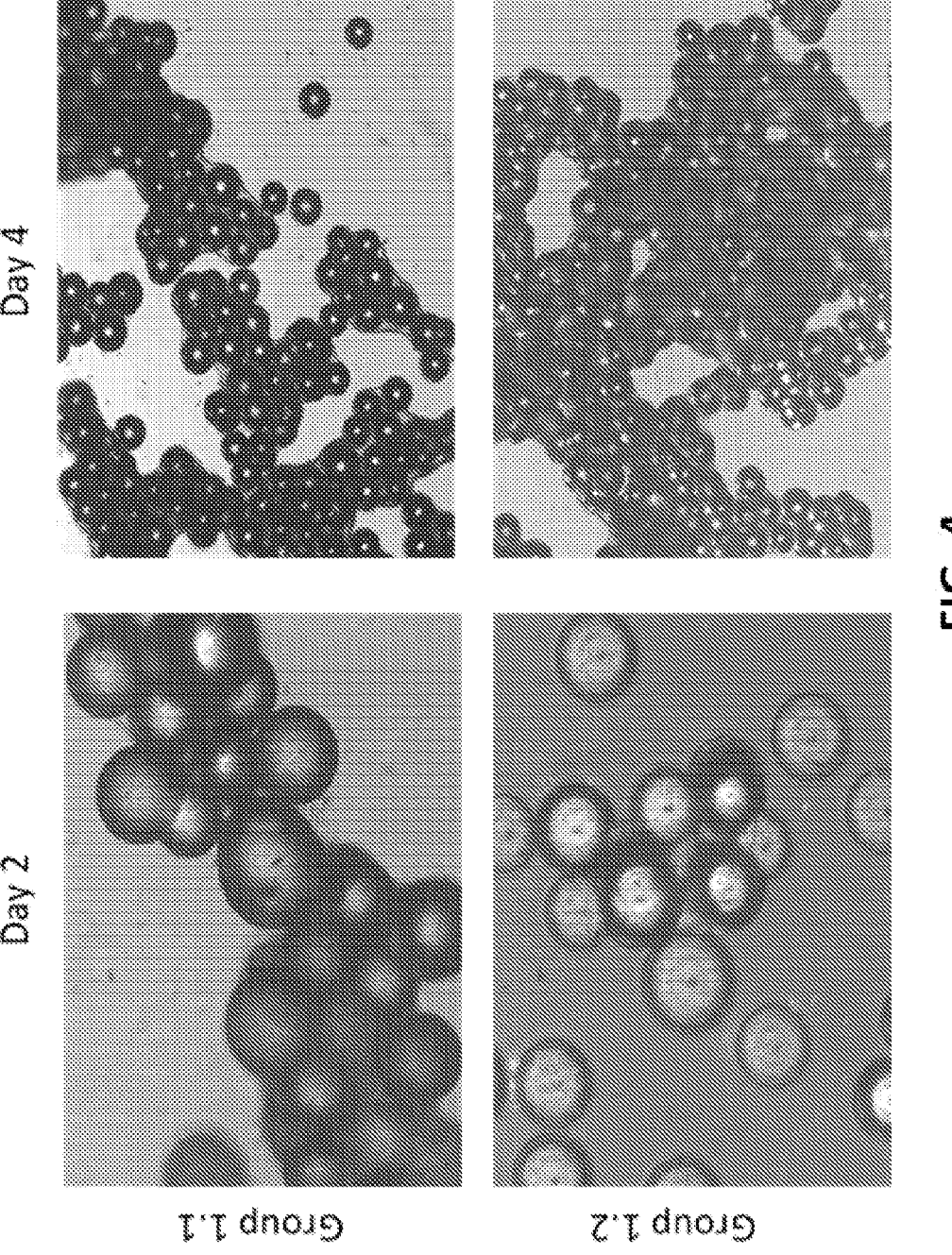
FIG. 4 shows the morphology of cells in the hESC scale-up system.

Morphology assessment of the hESC expansion scale-up system from both groups presented in Table 7 is presented in FIG. 4.

Lactate elevation in culture media between days 2 to 4 in addition to harvesting density, yield and expression of pluripotency markers in cells one passage post culturing in the hESC expansion scale-up system are presented in Table 8.

TABLE 8

Culturing parameters and pluripotency marker expression of cells cultured in the hESC scale-up system.

| Group # | Lactate on day 2 (mM) | Lactate on day 4 (mM) | Harvesting density (live cells/cm²) | Yield | % Of SSEA-5/TRA-1-60 positive cells | % Of Oct-4/Nanog positive cells |
|---|---|---|---|---|---|---|
| 1.1 | 3.88 | 14.30 | 341,400 | 17.07 | 98.62 | 84.26 |
| 1.2 | 3.01 | 13.71 | 317,200 | 15.86 | 98.34 | 84.92 |

Figure 5:
FIG. 5 shows the morphology of harvested cells from the hESCs scale-up system after re-seeding as hESCs 2D culture.
Figure 5:
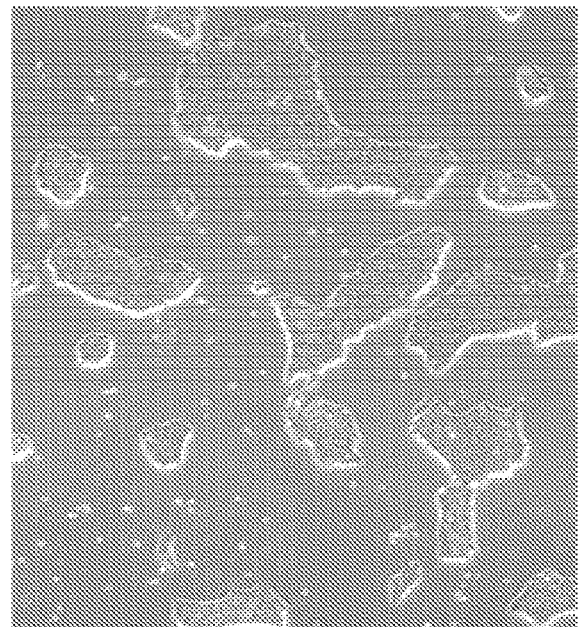

Morphology assessment of harvested cells seeded for further culturing is presented in FIG. 5. Cells are showing typical hESC morphology—organized as colonies of compact cells with a high ratio of nucleus to cytoplasm.

Cells were successfully cultured on Corning Synthemax® II and on Corning Enhanced Attachment MCs under hESC expansion scale-up system conditions and produced pluripotent hESCs.

Harvesting Method Prior to Inoculation of hESC Expansion Scale-Up System

Figure 3:
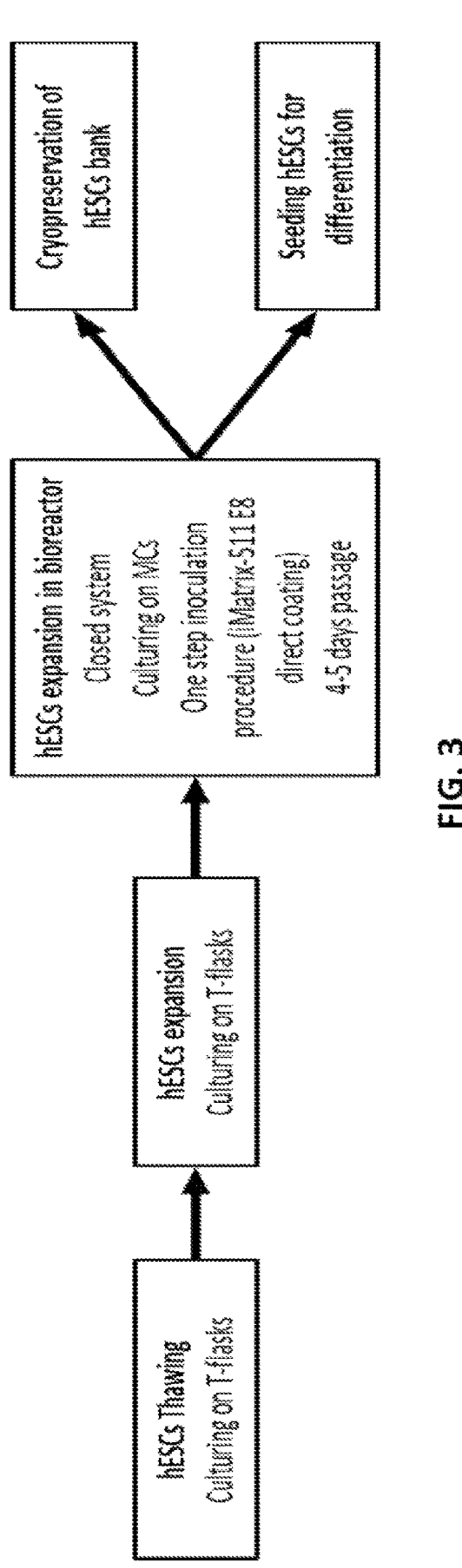
FIG. 3 shows the hESC expansion scale-up system process.

The full process, as presented in FIG. 3, involves culturing of hESCs as a 2D culture before inoculation to the hESC expansion scale-up system. Two harvesting methods from a traditional feeder-free 2D culture (non-enzymatic—results in small clumps of cells, and enzymatic—results in single cells) were used, before hESC expansion scale-up system inoculation. Both harvesting methods were tested on both types of MCs mentioned above. Groups are presented in Table 9.

TABLE 9

Tested conditions (combination of MCs type and harvesting reagent prior to inoculation) in the hESC scale-up system.

| Group # | MCs | Harvesting Reagent Prior to Inoculation | iMatrix-511-E8 concentration (ug/cm²) |
|---|---|---|---|
| 2.1 | Corning Synthemax ® II | ReLeSR (small clumps) | 0.125 |
| 2.2 | Corning Synthemax ® II | TrypLE Select (single cells) | 0.125 |
| 2.3 | Corning Enhanced Attachment | ReLeSR (small clumps) | 0.125 |

TABLE 9-continued

Tested conditions (combination of MCs type and harvesting reagent prior to inoculation) in the hESC scale-up system.

| Group # | MCs | Harvesting Reagent Prior to Inoculation | iMatrix-511-E8 concentration (ug/cm²) |
|---|---|---|---|
| 2.4 | Corning Enhanced Attachment | TrypLE Select (single cells) | 0.125 |

Figure 6:
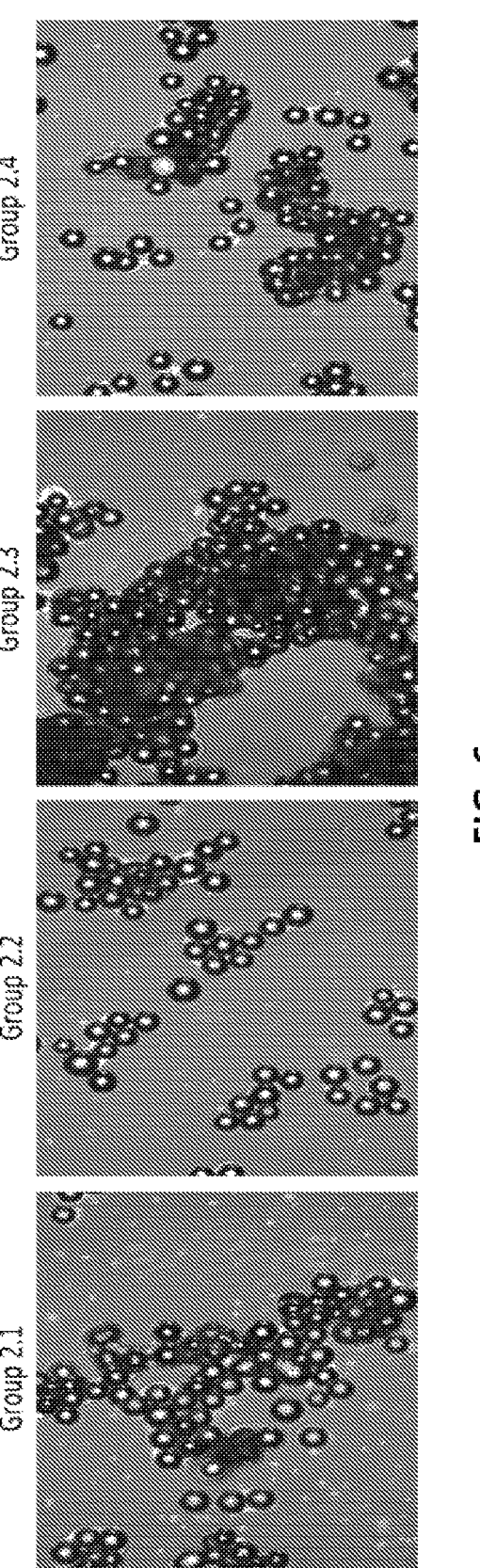
FIG. 6 shows the morphology of the hESC scale-up system under the tested conditions.

Morphology assessment of the hESC expansion scale-up system culturing Table 9 is presented in FIG. 6. In addition, culturing parameters and pluripotency marker expression of cells from all groups are presented in Table 10.

TABLE 10

Culturing parameters and pluripotency marker expression of cells cultured in the hESC scale-up system.

| Group # | Lactate on day 2 (mM) | Lactate on day 4 (mM) | Harvesting density (live cells/cm²) | Yield | % Of SSEA-5/TRA-1-60 positive cells | % Of Oct-4/Nanog positive cells |
|---|---|---|---|---|---|---|
| 2.1 | 4.22 | 12.22 | 302,000 | 15.10 | 96.88 | 86.23 |
| 2.2 | 1.25 | 4.20 | 34,500 | 0.69 | 97.56 | 97.66 |
| 2.3 | 4.53 | 14.31 | 378,000 | 18.90 | 97.59 | 94.54 |
| 2.4 | 2.16 | 8.11 | 184,000 | 3.68 | 98.05 | 97.79 |

Expression of pluripotency markers (>86% positive for all tested markers), lactate concentration elevation during culturing, added to harvesting density and yield showed that harvesting cells before inoculation in the hESC expansion scale-up system was accomplished with ReLeSR as well as with TrypLE Select. Both methods are suitable for hESC harvesting prior to inoculation in the hESC expansion scale-up system.

Both MCs (Corning Synthemax® II and Corning Enhanced attachment) and both harvesting methods (ReLeSR and TrypLE Select) are suitable for the hESC expansion scale-up system. Moreover, based on the data shown above, it is rational to assume that culturing hESCs harvested with TrypLE Select from MCs and seeded for additional passage in the hESC expansion scale-up system is feasible.

Culturing Platforms for the hESC Expansion Scale-Up System

Expansion of hESCs in the hESC expansion scale-up system was tested in different culturing platforms and in different working volumes and MC surface areas. Examples for several culturing platforms are presented in Table 11.

TABLE 11

Platforms for culturing in the hESC scale-up system.

| Group # | MCs | Vessel | MCs surface area (cm²) | Medium Volume (ml) | iMatrix-511-E8 concentration (ug/cm²) |
|---|---|---|---|---|---|
| 3.1 | Corning Enhanced Attachment | Non-Treated T25 | 25 | 10 | 0.125 |
| 3.2 | Corning Enhanced Attachment | 0.1L PBS wheel | 125 | 50 | 0.125 |
| 3.3 | Corning Enhanced Attachment | 0.1L PBS wheel | 250 | 100 | 0.125 |
| 3.4 | Corning Enhanced Attachment | 0.5L PBS wheel | 625 | 250 | 0.125 |
| 3.5 | Corning Enhanced Attachment | 0.5L PBS wheel | 1,250 | 500 | 0.125 |

TABLE 11-continued

| Platforms for culturing in the hESC scale-up system. | | | | |
|---|---|---|---|---|
| Group # MCs | Vessel | MCs surface area (cm²) | Medium Volume (ml) | iMatrix-511-E8 concentration (ug/cm²) |
| 3.6 Corning Enhanced Attachment | 3L PBS-MAG closed system | 7,500 | 3,000 | 0.125 |

Figure 7:
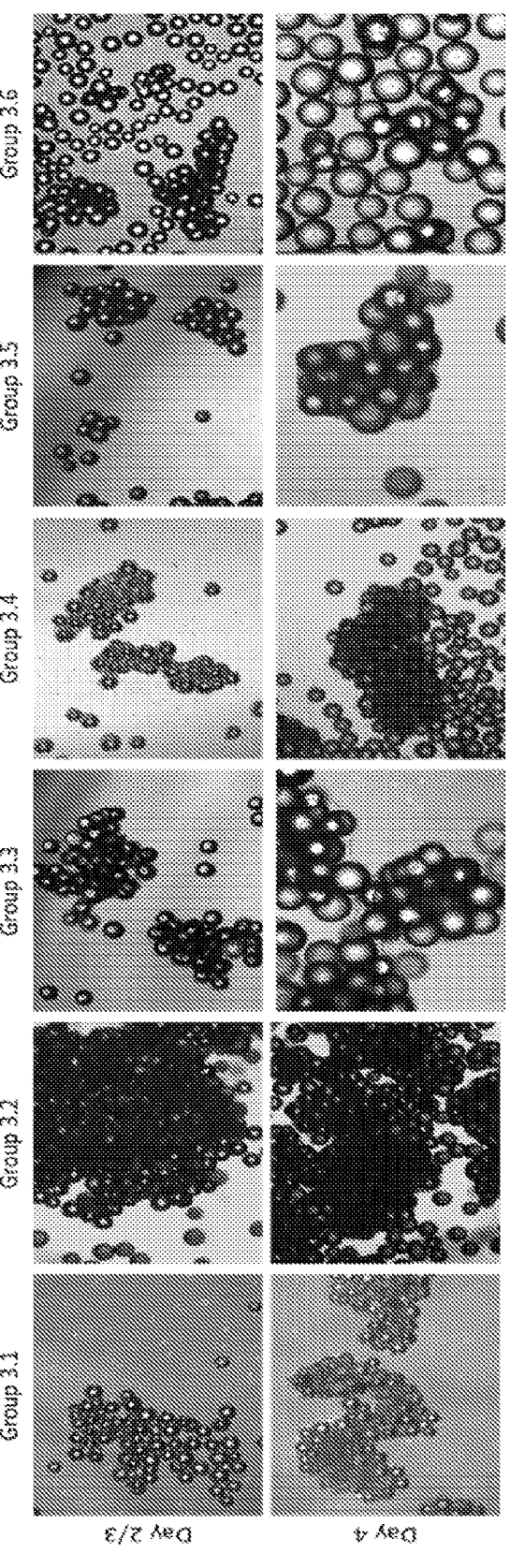
FIG. 7 shows the morphology of the hESC scale-up system in different platforms.

Morphology assessment of the hESC expansion scale-up system from the platforms in Table 11 is presented in FIG. 7.

Culture growth was assessed by measuring lactate concentration along culturing. In addition, harvesting density and yield were calculated. The identity and pluripotency of hESCs was evaluated at the end of culturing by flow cytometry analysis of pluripotency marker expression. In addition, during development, the karyotype of the harvested cells from the hESC expansion scale-up system was tested. Results are summarized in Table 12.

TABLE 12

| | Culturing parameters and pluripotency marker expression of cells cultured in the hESC scale-up system. | | | | | | |
|---|---|---|---|---|---|---|---|
| Group # | Lactate on day 2 (mM) | Lactate on day 4 (mM) | Harvesting density (live cells/cm²) | Yield | % Of SSEA-5/TRA-1-60 positive cells | % Of Oct-4/Nanog positive cells | Karyotype |
| 3.1 | 5.78 | 18.89 | 520,000 | 20.80 | 99.87 | 95.41 | Normal |
| 3.2 | 9.33 | 15.33 | 371,200 | 18.56 | 99.73 | 92.76 | NA |
| 3.3 | 4.36 | 13.23 | 329,200 | 13.17 | 99.95 | 96.90 | Normal |
| 3.4 | 6.47 | 10.37 | 228,400 | 11.42 | 99.87 | 96.48 | NA |
| 3.5 | 3.39 | 11.78 | 254,000 | 16.93 | TBD | TBD | TBD |
| 3.6 | 2.25 | 5.03 | NA | NA | TBD | TBD | NA |

Growth of hESCs in the hESC expansion scale-up system was accomplished in several culturing vessels (non-treated T25, 0.1L PBS wheel, 0.5L PBS wheel, 3L PBS-MAG) in different MCs surface areas (25 cm², 125 cm², 250 cm², 625 cm², 1,250 cm² and 7,500 cm²) and working volumes (10 mL, 50 mL, 100 mL, 250 mL, 500 mL, 3,000 mL). Culturing in the hESC expansion scale-up system led to maintenance of very high expression of pluripotency markers even after changing the culturing vessels and conditions.

iMatrix-511 E8 Concentration for Efficient Inoculation

Figure 8:
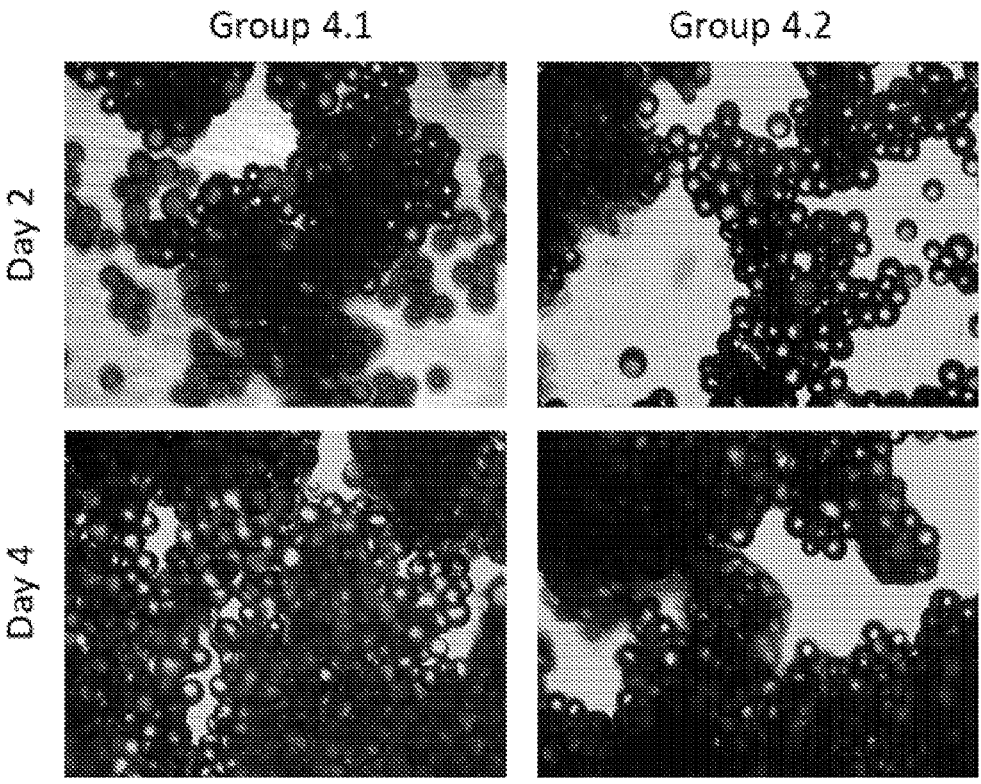
FIG. 8 shows the morphology of the hESC scale-up system with different iMatrix-511 E8 concentrations.

The hESC expansion scale-up system inoculation was performed with two iMatrix-511 E8 concentrations. The conditions tested and cell growth (assessed by increase in lactate concentration between days 2 and 4 of 4 days passage, and by cells-MCs clumps formation) are summarized in Table 13 and in FIG. 8.

TABLE 13

| | iMatrix-511 E8 concentration during inoculation in the hESC scale-up system. | | | |
|---|---|---|---|---|
| Group # | MCs | iMatrix-511-E8 concentration (ug/cm²) | Lactate on day 2 (mM) | Lactate on day 4 (mM) |
| 4.1 | Corning Enhanced Attachment | 0.125 | 5.85 | 15.72 |

TABLE 13-continued

| | iMatrix-511 E8 concentration during inoculation in the hESC scale-up system. | | | |
|---|---|---|---|---|
| Group # | MCs | iMatrix-511-E8 concentration (ug/cm²) | Lactate on day 2 (mM) | Lactate on day 4 (mM) |
| 4.2 | Corning Enhanced Attachment | 0.250 | 5.98 | 16.53 |

Expansion of hESCs in the hESC expansion scale-up system was accomplished when using 0.125 and 0.250 ug/cm² of iMatrix-511 E8 during inoculation. Moreover, based on the data shown above, it can be projected that iMatrix-511 E8 concentration of 0.125-0.250 ug/cm² will result in efficient growth of hESCs in the hESC expansion scale-up system.

Passage Duration of hESCs on MCs in the hESC Expansion Scale-Up System

Figure 9:
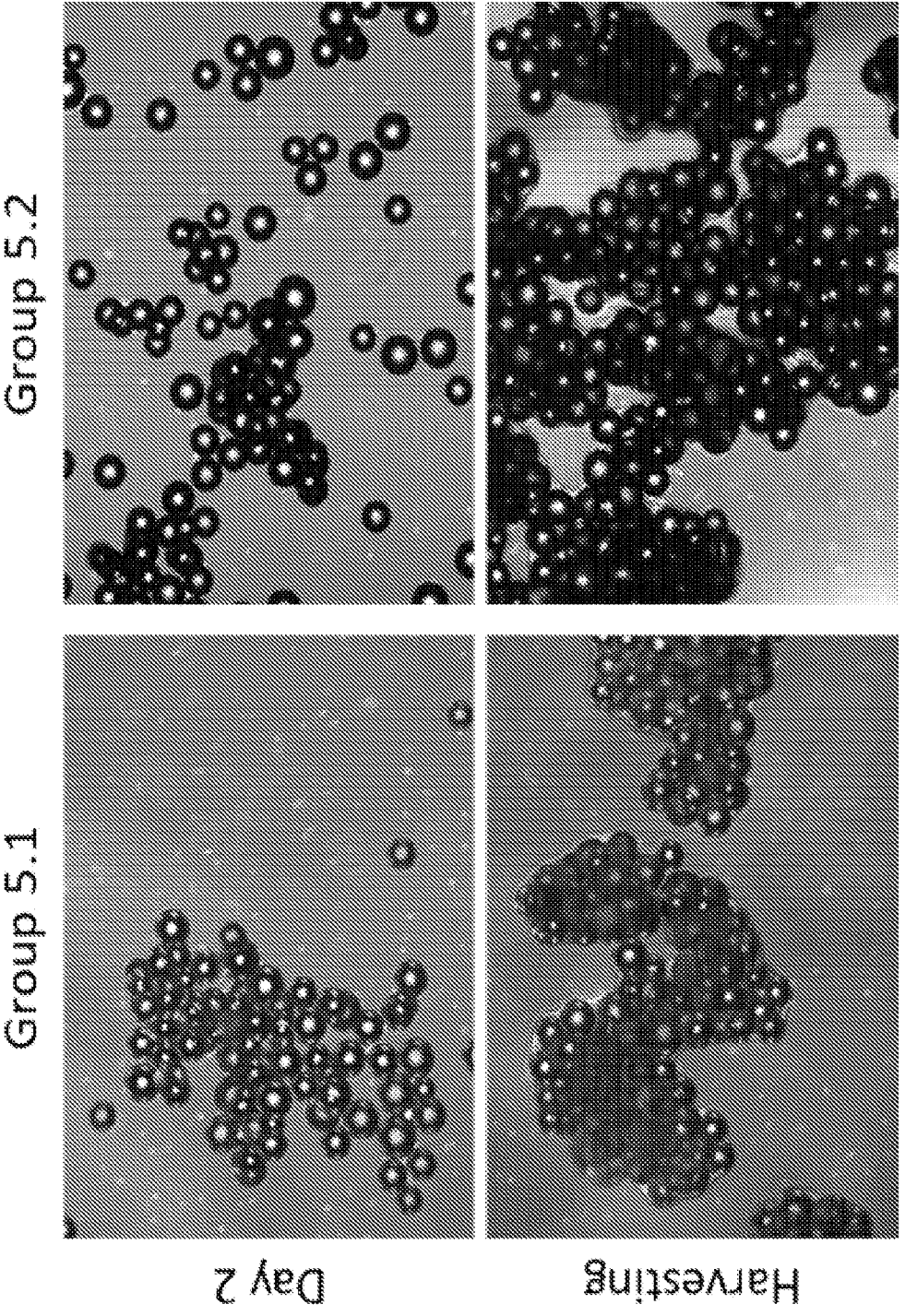
FIG. 9 shows the morphology of the hESC scale-up system in different passage durations.

To allow flexibility for hESC culturing in the hESC expansion scale-up system, 4- and 5-day passages were evaluated. Adjustment of hESC seeding density for different passage durations was performed. Comparison of harvesting density, lactate at harvesting, morphology and pluripotency marker expression of hESCs harvested post 4-day passage (group 5.1) and 5-day passage (group 5.2) is presented in Table 14 and in FIG. 9. Morphology assessment and lactate at harvesting showed similarity between 4- and 5-day passage culturing. In addition, pluripotency marker expression was high in both groups (>89% for all markers).

TABLE 14

Culturing parameters and pluripotency markers expression
of cells cultured in hESCs scale-up system.

| Group # | Passage duration (days) | Seeding density (live cells/cm$^2$) | Lactate on day 2 (mM) | Lactate at harvesting (mM) | Harvesting density (live cells/cm$^2$) | Yield | % Of SSEA-5/TRA-1-60 positive cells | % Of Oct-4/Nanog positive cells |
|---|---|---|---|---|---|---|---|---|
| 5.1 | 4 | 25,000 | 5.78 | 18.89 | 520,000 | 20.80 | 99.87 | 95.41 |
| 5.2 | 5 | 6,500 | 2.96 | 17.71 | 475,200 | 73.11 | 99.68 | 89.44 |

For both the 4- and 5-day passage duration, hESC culturing in the hESC expansion scale-up system was accomplished. By adjusting the seeding density according to passage duration, hESC cultures reached similar lactate concentration and harvesting density. Moreover, by adjusting the seeding density, culturing hESCs on MCs in the hESC expansion scale-up system can be accomplished for 3-7 day passages.

Figure 10:
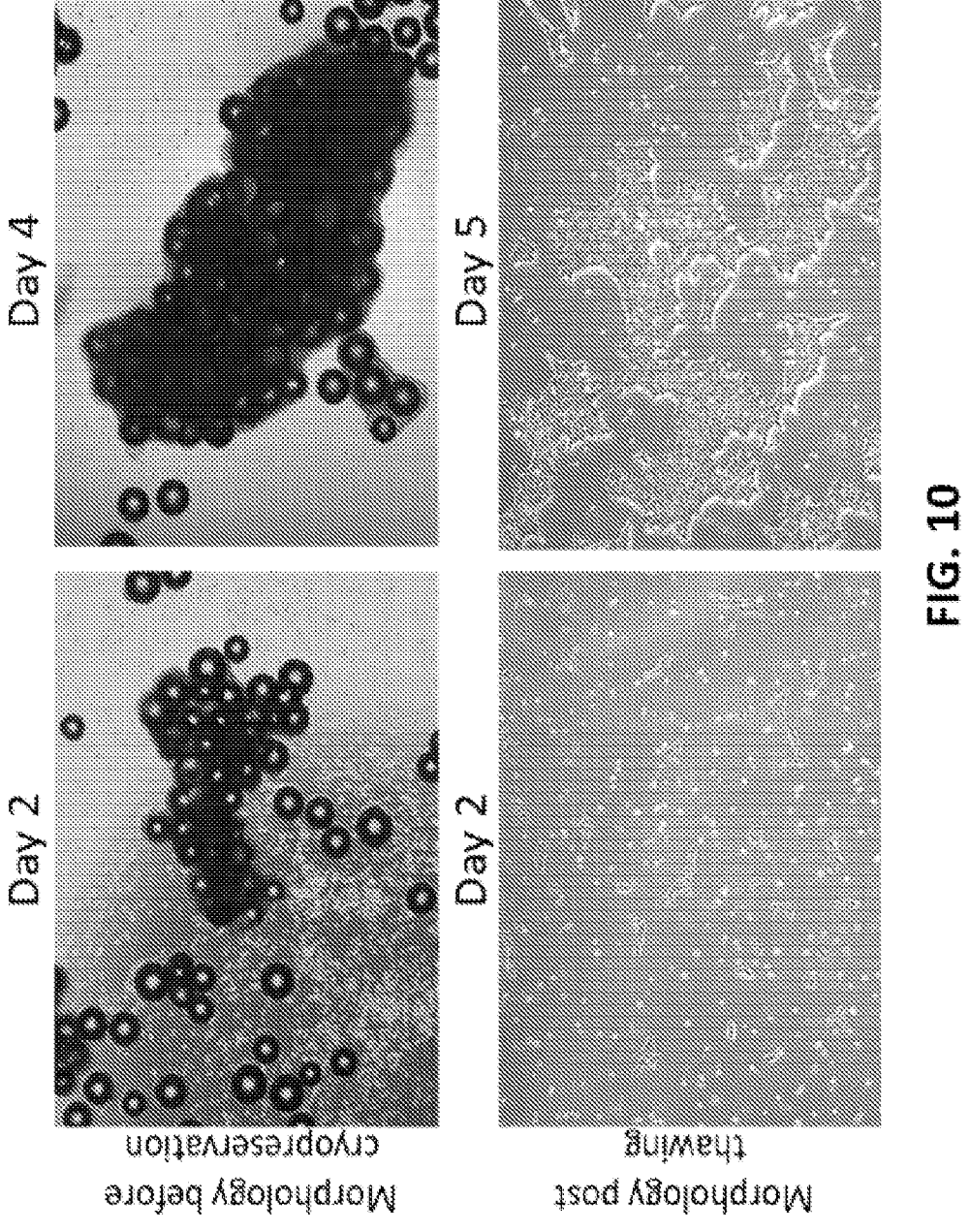
FIG. 10 shows the morphology of cells cultured in the hESC scale-up system before cryopreservation and after thawing as 2D culture.

Cryopreservation of the hESC Bank from Cells Cultured in the hESC Expansion Scale-Up System Harvested cells from the hESC expansion scale-up system were cryopreserved. Then, thawed cells were tested for pluripotency marker expression and seeded for further culturing as a 2D traditional feeder-free culturing. The thawed cells showed high pluripotency marker expression (Table 15) in addition to maintaining hESC morphology post culturing in the hESC expansion scale-up system. Culturing parameters in the hESC expansion scale-up system and pluripotency marker expression are presented in Table 15. Morphology of cells during culturing on MCs in the hESC expansion culturing system in addition to 2- and 5-day post thawing and seeding on 2D feeder-free traditional flasks for follow-up are presented in FIG. 10.

TABLE 15

Culturing parameters and pluripotency marker expression
of cells cultured in the hESC scale-up system.

| Group # | Lactate on day 2 (mM) | Lactate on day 4 (mM) | Harvesting density (live cells/cm$^2$) | Yield | % Of SSEA-5/TRA-1-60 positive cells | % Of Oct-4/Nanog positive cells |
|---|---|---|---|---|---|---|
| 6.1 | 4.26 | 15.31 | 352,800 | 17.64 | 98.97 | 95.80 |

Cryopreservation of the hESC bank from the hESC expansion scale-up system cells was accomplished. Cells showed high expression of pluripotency markers (>95% positive for all tested markers) in addition to maintaining hESC typical morphology as a 2D culture after re-seeding of the thawed cells.

Figure 11:
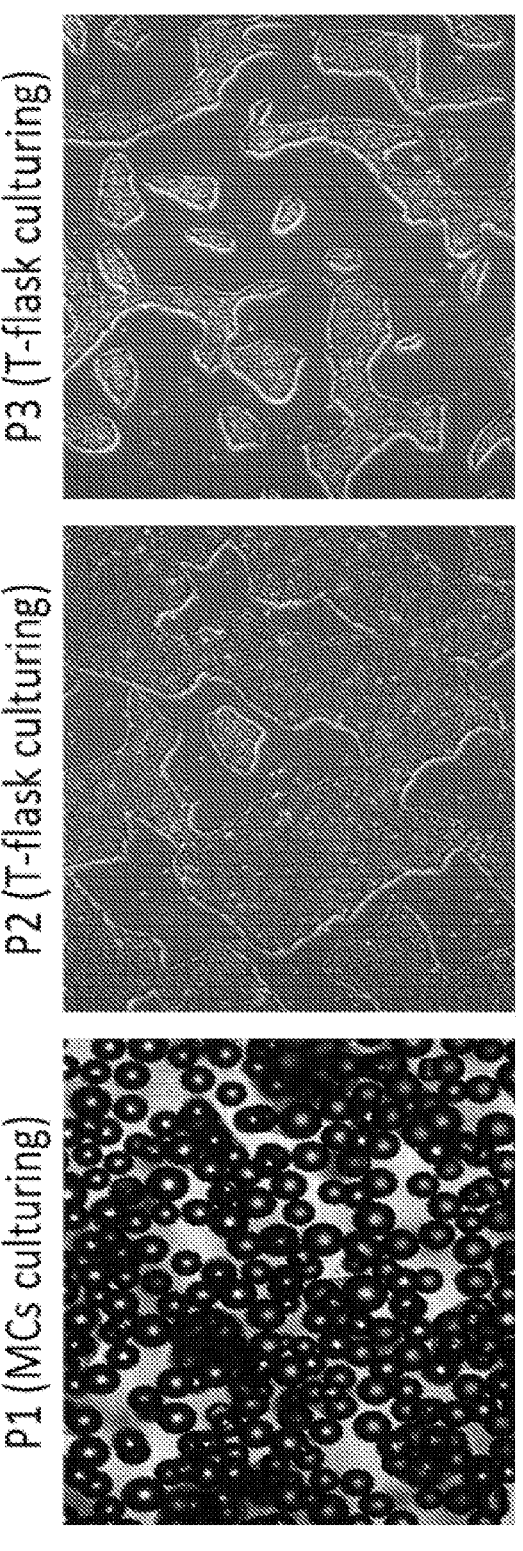
FIG. 11 shows culturing parameters and pluripotency marker expression of cells cultured in the hESCs scale-up system and passaged as 2D culture.

Further Culturing of Harvested Cells from the hESC Expansion Scale-Up System as 2D hESC Culture Harvested cells from the hESC expansion scale-up system can be further expanded as a hESC 2D culture. In the following example, cells harvested from the hESC expansion scale-up system were further cultured as a 2D feeder-free traditional culturing. Culturing parameters (lactate at harvesting) in addition to morphology of cells cultured in the hESC expansion scale-up system and as 2D culture for 2 consecutive passages are presented in Table 16 and in FIG. 11.

TABLE 16

Culturing parameters and pluripotency marker expression
of cells cultured in the hESC scale-up system
and further passaged as 2D culture.

| Group # | Passage (culturing on MCs was referred as 1) | Lactate at harvesting (mM) | Harvesting density (live cells/cm$^2$) | Yield | % Of SSEA-5/TRA-1-60 positive cells | % Of Oct-4/Nanog positive cells |
|---|---|---|---|---|---|---|
| 7.1 | 1 (MCs culturing) | 7.57 | 187,200 | 9.36 | 99.67 | 94.72 |
| | 2 (T-flask culturing) | 13.21 | 387,600 | 19.38 | NA | NA |
| | 3 (T-flask culturing) | 8.55 | NA | NA | NA | NA |

Harvested cells from the hESC expansion scale-up system showed high pluripotency marker expression (>94% for all tested markers). In addition, typical morphology of hESCs was observed in culture in both 2D further passages. Further culturing of harvested cells from the hESC expansion scale-up system on iMatrix-511 E8 direct coated flasks was accomplished.

Differentiation of Harvested Cells from the hESC Expansion Scale-Up

The main characteristic of pluripotent stem cells is the potential to differentiate into all three germ layers. Harvested cells from the hESC expansion scale-up system were seeded and differentiated into dendritic cells according to established protocol. Dendritic cell marker expression at the end of differentiation is presented in Table 17.

TABLE 17

DC marker expression of cells derived from harvested
cells from the hESC scale-up system.

| | Marker expression at the end of DC differentiation | | | |
|---|---|---|---|---|
| Group # | % CD45 | % CD86 | % CD83 | % CD40 |
| 8.1 | 97.60 | 97.60 | 93.50 | 95.60 |

Figure 2:
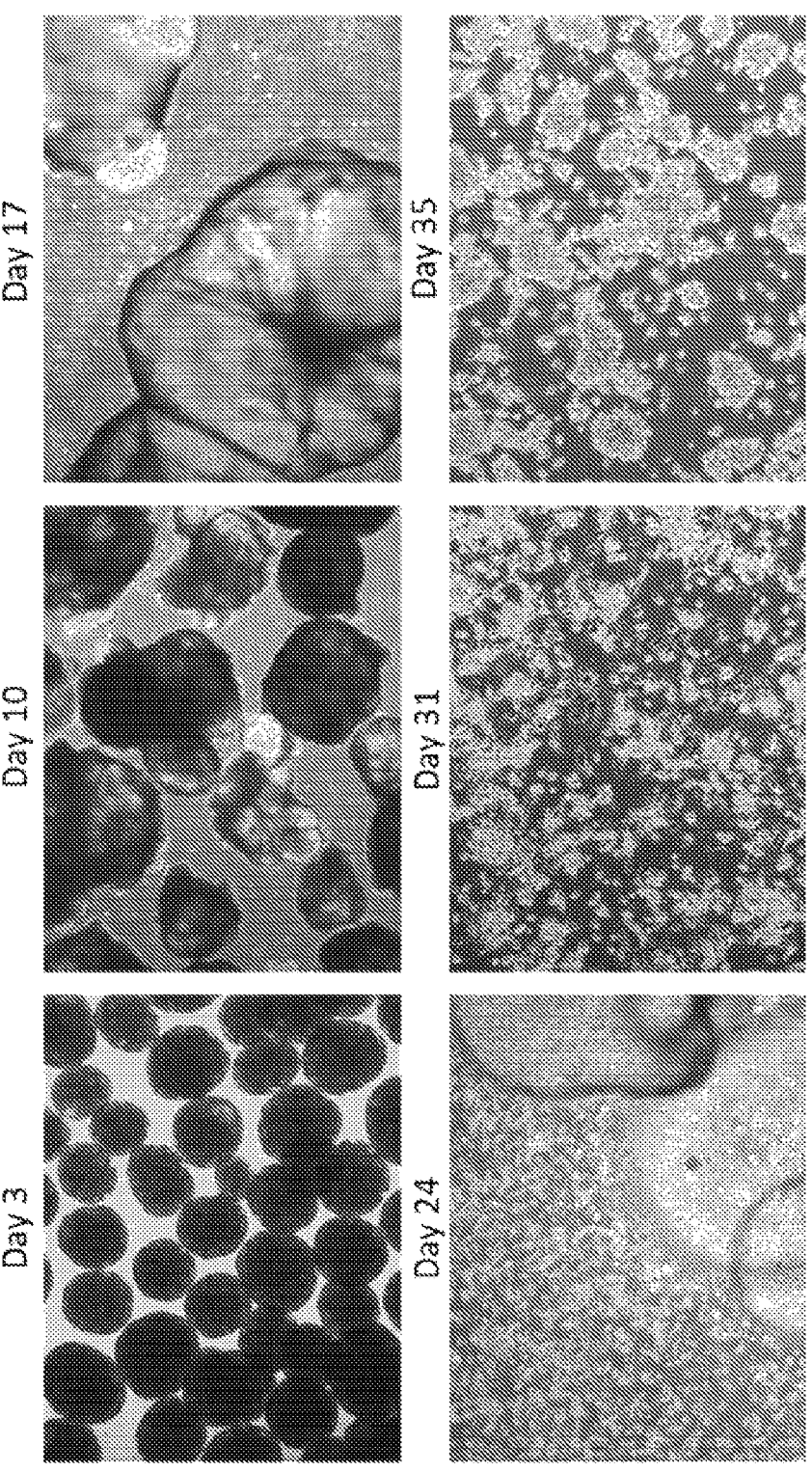
FIG. 2 shows morphology of harvested cells from the hESC scale-up system during DC differentiation.

Morphology assessment of cells along dendritic cells differentiation process is presented in FIG. 2.

Differentiation of cells harvested from the hESC expansion scale-up system into dendritic cells was accomplished efficiently. Differentiation of harvested cells from the hESC expansion scale-up system into any lineage and cell type can be assumed to be enabled from the hESC expansion scale up system cells with or without harvesting.

What is claimed is:

1. A method for expanding and maintaining human stem cells in an undifferentiated, pluripotent state, the method comprising the steps of (a) simultaneously combining human stem cells, human laminin 511 E8 fragment, and polystyrene microcarriers in growth medium to form a suspendable expansion complex, and (b) culturing the suspendable expansion complex for a period of time, thereby producing cultured cells.

2. The method of claim 1, wherein the polystyrene microcarriers comprise one or more of polystyrene, cross-linked dextran, magnetic particles, microchips, cellulose, hydroxylated methacrylate, collagen, gelatin, plastic, glass, ceramic, silicone, or a combination thereof.

3. The method of claim 1, wherein the polystyrene microcarriers are spherical, smooth, macroporous, rod-shaped, or a combination thereof.

4. The method of claim 1, wherein the polystyrene microcarriers are not coated.

5. The method of claim 1, wherein the polystyrene microcarriers are coupled with protamine or polylysine.

6. The method of claim 1, wherein the polystyrene microcarriers are neutral or negatively charged.

7. The method of claim 1, wherein the polystyrene microcarriers are hydrophilic.

8. The method of claim 1, wherein the suspendable expansion complex is cultured for at least about one day.

9. The method of claim 8, wherein the suspendable expansion complex is cultured from about one day to about fourteen days.

10. The method of claim 1, wherein the cultured cells of the suspendable expansion complex are harvested and expanded further by repeating steps (a) and (b).

11. The method of claim 1, wherein the cultured cells of the suspendable expansion complex are harvested and further differentiated.

12. The method of claim 11, wherein the cultured cells of the suspendable expansion complex are further differentiated by changing the growth medium.

13. The method of claim 1, wherein the cultured cells of the suspendable expansion complex remain undifferentiated and pluripotent.

14. The method of claim 1, wherein at least about 80% of the cultured cells express each of SSEA-5 and TRA-1-60.

15. The method of claim 1, wherein at least about 70% of the cultured cells express each of Oct-4 and Nanog.

16. The method of claim 1, wherein at least about 80% of the cultured cells express SSEA-5, at least about 80% of the cultured cells express TRA-1-60, at least about 70% of the cultured cells express Oct-4, and at least about 70% of the cultured cells express Nanog.

17. The method of claim 1, wherein the human stem cells are induced pluripotent stem cells (iPSCs) or human embryonic stem cells.

18. The method of claim 1, wherein the polystyrene microcarriers are surface treated with infused oxygen.

* * * * *